United States Patent [19]
Halliday

[11] Patent Number: 5,435,193
[45] Date of Patent: Jul. 25, 1995

[54] SYSTEM AND METHOD FOR MEASURING THE GRIP PERFORMANCE OF A VEHICLE

[76] Inventor: Donald R. Halliday, 5312 Cascade Dr., Powell, Ohio 43065

[21] Appl. No.: 220,740

[22] Filed: Mar. 31, 1994

[51] Int. Cl.⁶ .......................................... G01M 17/04
[52] U.S. Cl. ................... 73/862.541; 280/688
[58] Field of Search ............ 73/862.041, 862.042, 73/862.043, 862.05, 862.541

[56] References Cited

U.S. PATENT DOCUMENTS

| | | | |
|---|---|---|---|
| 3,713,330 | 1/1973 | Lentz | 73/862.043 |
| 4,371,191 | 2/1983 | Goldberg et al. | 280/707 |
| 4,588,198 | 5/1986 | Kanazawa et al. | 280/90 |
| 4,843,873 | 7/1989 | Harald et al. | 73/862.041 |
| 5,025,879 | 6/1991 | Mitsunari | 180/79 |
| 5,186,042 | 2/1993 | Miyazaki | 73/862.041 |
| 5,251,719 | 10/1993 | Eto et al. | 180/197 |
| 5,265,946 | 11/1993 | Bader | 303/96 |

Primary Examiner—Richard E. Chilcot, Jr.
Assistant Examiner—Eric S. McCall
Attorney, Agent, or Firm—Mueller and Smith

[57] ABSTRACT

A system and a method are disclosed for measuring the grip performance of a vehicle through relation to a lumped-sum parameter derived from force and displacement measurements taken from selected elements forming the suspension of the vehicle. For at least one wheel of the vehicle, the magnitude and relative direction of the instantaneous load force vector acting on each support member thereof are measured. The load force vectors are resolved with respect to a relative plane into a first load force component, a second load force component normal to said first component, and a third load force component normal to said first and said second component. The load force components then are related to a common reference plane to derive normalized load force components, which normalized components then are summed to derive total normalized first, second, and third load force components which correspond to the instantaneous grip force developed between the wheel of the vehicle and the ground surface.

33 Claims, 24 Drawing Sheets

SYSTEM AND METHOD FOR MEASURING THE GRIP PERFORMANCE OF A VEHICLE

BACKGROUND OF THE INVENTION

The present invention relates to a system and method for measuring the grip performance of a vehicle, such as a passenger car, a racing car, a motorcycle, or the like, through relation to a lumped-sum parameter derived from force and linear and/or angular displacement measurements taken from selected elements forming the suspension of the vehicle. In deriving this parameter as representative of the time dependent grip forces developed between the tire of the car and the surface of the road, the present invention establishes a criteria for comparing and optimizing the ultimate effects of mechanical and aerodynamic changes or adjustments made in the car or to its components, and additionally allows for the determination of the absolute values of the forces acting upon each wheel of the car and for the comparison of road surface grip.

The measurement of what may be termed as the "performance" of a car is a problem which has long perplexed both the car engineer and the tire designer alike. Broadly, the overall performance of a car may be based on any or all of its front and rear braking, acceleration, and cornering response. Improvements in performance may be effected by improving the fixed mechanical and aerodynamic design parameters of the car, and/or by dynamically compensating for inadequacies in such design by using computationally controlled corrective systems such as and-locking brakes, traction control, and active ride height systems. Thus far, however, the performance analysis of the design or corrective system has lagged behind the design itself for want of analytical data and criteria upon which an improvement in performance might be determined. Complicating the matter is that the individual responses which combine to give a car its overall performance each depend not on one parameter, but ultimately upon a complex, three-dimensional interaction between innumerable variables such as: the design and construction of the tires; the design of the mechanical systems, chassis, suspension, and frame including mass distribution and aerodynamic effects; and the road and driving conditions including the road surface and ambient temperature. The interactive effects of each of these variables must be considered by any system which would be capable of measuring car performance.

Heretofore, attempts at measuring and managing car performance have focused either on subjective "seat of the pants" and trial-and-error techniques, or more recently on complex computational modeling directed to simulate at least some of the interactive variables affecting the braking, acceleration, and cornering responses of the car. The complexities of the interactions between those variables, however, have proved unmanageable at best to even approximate car performance. For example, even with the mechanical systems and aerodynamic components of a given car left unchanged, such transient phenomena as variations in road or track and ambient conditions appreciably affect car performance to a degree, at least in auto racing, which can be the measure between winning and losing. As illustrative of the complexities involved in computationally modeling car performance, Table I lists only a few of the elements which must be considered as affecting the grip, balance, or drag of the car.

TABLE I

| System or Condition | Variable or Measurement |
|---|---|
| Tires | Instantaneous camber as affected by camber change characteristics, static settings, car roll, car structural integrity, Ackerman steering geometry, steering angle, and tire load |
| | Instantaneous toe in or out as affected by dynamic toe change, static toe setting, car structural integrity, and tire load |
| | Instantaneous tire pressure |
| | Tire mileage or wear as affecting acceleration, lateral cornering, and steady-state running. |
| | Tire temperature and temperature distribution |
| Mechanical | Weight distribution and front and rear sprung and unsprung weight as affected by fuel load and component wear |
| | Front and rear track width |
| | Height of sprung and unsprung center of mass |
| | Torsional rigidity of car front to rear at center line as affected by temperature and instantaneous structural stresses |
| Aerodynamic (Racing) | Front wing mainplane proximity to ground and angle |
| | Left and right flap angles and front wing skirt positions |
| | Front and rear brake duct type |
| | Front and rear wing, and under wing gurney lip configuration |
| | Rear wing type and angle |
| | Engine RPM as affecting underwing exit because of exhaust gases |
| | Radiator type and inlet and exit opening detail |
| | Engine inlet detail |
| | Proximity of rear wheel to bodywork |
| | Roll hoop and windscreen type, height, and detail |
| Setup Adjustments | Front and rear springs, suspension, and anti roll bar wheel rates |
| | Front and rear shock absorbers valving bump and release low and high speed rates |
| | Front left and right side caster |
| | Instantaneous front and rear ride height and roll center position |
| | Dynamic car cross weight |
| | Rear tire staggered diameters |
| Ambient Conditions | Track or road temperature and surface type and condition |
| | Air temperature |

Nowhere is the gap between performance design and performance analysis as evident as in the sport of auto racing. In most classes of auto racing, and especially with "Indy" cars, there exists an anomaly in that car specifications are intentionally made restrictive to force a competitive similarity in approach to both car design and performance. Unfortunately, at least from the standpoint of the engineer or designer, the upper echelons of competitive auto racing, including both "Indy" or CART and Formula 1, have or will have banned the use of closed-loop systems for controlling the corrective systems of the car. The need, therefore, to optimize the performance of the car during its design and pre-race tuning or setup stages now has become even more critical to achieving consistently fast lap times. Indeed, there has been seen performance fluctuations as between teams running the same make of car, and even as within the same team on different days or on different tracks.

Currently the braking, acceleration, and cornering performance of race cars are determined at the track in terms of corner speeds and split times, dynamic ride height change, longitudinal and lateral accelerations, shock displacements, and engine and tire temperatures and pressures. None of this data, however, definitively provides a quantitates measurement of the determinative factor of car performance, that of the grip force. Accordingly, it is ultimately the driver who now is called upon to subjectively judge the relative, performance of the car on any one day and in response to what may be the cumulative effects of a plethora of design changes or adjustments, or simply a change in track or ambient conditions. With different drivers, however, come different "seat of the pants" opinions as to the level of car performance. Even as to the same driver, his or her experience level and present state of mind affects perceptions and precludes there being any comparative standard upon which the engineer or designer might objectively base performance.

In view of the foregoing, it is apparent that there has existed and remains a need in both the sport of auto racing and in the passenger car industry for a means to optimize, in some objective and predictable manner, all the setup and design variables which ultimately interact to determine the overall performance of the car. Preferably, such means would provide some criteria for objectively comparing and endorsing of the incremental effects on overall performance of changes, improvement, or adjustments made to the mechanical or aerodynamic packages of the car. The preferred means also would consider or be unaffected by such transient phenomena as changes in ambient conditions or road surface type or condition, and additionally would provide a capability for determining the absolute values of the forces acting upon each wheel of the car. Such means would be welcomed by: the design engineer in analytically measuring and comparing the performance of various tire, suspension, mechanical, aerodynamic, and engine designs; by the track or race engineer in tuning and optimizing the setup parameters of the racing car prior to a run; and by the driver in allowing for the design of various closed-loop control, warning, or safety systems which, for example, might be linked to engine speed for enabling safe cornering operation.

BROAD STATEMENT OF THE INVENTION

The present invention is directed to a system and method for measuring the grip or roadholding performance of a vehicle, such as a passenger or racing car or the like, through relation to a lumped-sum parameter derived from force and linear and/or angular displacement measurements taken from selected elements forming the suspension of the vehicle. It has been discovered that it is the frictional grip force reaction in the contact patch defining the interface between the wheel or fire of the car and the surface of the road which ultimately is the determining factor in the dynamic performance of car in terms of its braking, acceleration, and cornering. In providing for a system and method which generate meaningful force vectors representative of the time-dependent lateral, longitudinal, and vertical grip forces developed between the road and each tire, the present invention is able to thereby establish a criteria for objectively comparing and optimizing the effects of mechanical or aerodynamic adjustments made to the car. Moreover, in directly measuring the performance of a car in terms of the grip force at the contact patch of each of its tires rather than by trying to predict such result through computational modeling, the present invention is seen as unaffected by transient phenomena which could not be accounted for through mere simulation. Coupled with the measurement of the lateral centripetal or centrifugal forces, and the longitudinal lift and vertical drag aerodynamic forces operating upon the wheel or tire of the vehicle, the present invention additionally allows for a true force balance on each wheel for obtaining absolute values of the forces acting thereon.

The system and method of the invention involve the dynamic measuring of the force vectors acting upon selected elements forming the suspension of the vehicle, which force vectors have been discovered to directly relate to the grip or frictional roadholding performance of the vehicle. The measurements are acquired using a combination of force measurement systems, strain gauges, and angular displacement or distance sensors which are mounted on the suspension elements and/or chassis of the vehicle to determine, for example, the vertical, lateral, and longitudinal forces acting on the support members attaching the wheel support system or upright to the chassis, on the toe link controls which steer the car on the front and which retain the uprights in toe to the chassis on the rear, and on spring, damper, shock, or pushrod supporting the chassis on the upright. From the dynamic or time-dependent measurement of these forces, the resultant force vectors are calculated and their components forces then are summed with relation, for example, to the directions acting between the tire and the road surface, namely, vertical to the road surface, transverse or lateral to the longitudinal center line of the car and in the plane of the road surface, and in the forward direction of car movement parallel to the longitudinal center line of the car and in the plane of the road surface. The summed components of the forces taken from the suspension members relate directly to the forces within the contact patches between the wheels of the vehicle and the surface of the road, and therefore provide a criteria for measuring the ultimate grip or roadholding performance of the vehicle.

The present invention, accordingly, comprises the system and method possessing the combination and arrangement of elements and steps which are exemplified in the following detailed disclosure. An advantage of the invention is the generation of a meaningful criteria representative of the time-dependent lateral, longitudinal, and vertical grip forces developed between the road and each tire. Such criteria facilitates the objective comparison and optimization of the effects of mechanical or aerodynamic adjustments made to the car, and also may be used in obtaining a true force balance on each wheel for determining the absolute values of the forces acting thereon. A further advantage of the invention is a capability to account for transient phenomena affecting the performance of the vehicle without having to computationally model such phenomena. These and other advantages and objects of the present invention will be readily apparent, in part, based upon the detailed disclosure which follows.

BRIEF DESCRIPTION OF THE DRAWINGS

For a fuller understanding of the nature and objects of the invention, reference should be had to the following detailed description taken in connection with the accompanying drawings wherein.

The drawings will be described further in connection with the following Detailed Description of the Invention.

DETAILED DESCRIPTION OF THE INVENTION

In the description to follow, the precepts of the present invention for are illustrated in connection with its use in first a road racing car, and then in a passenger car. However, in view of its utility and advantages, it will be understood that the present invention will find application in any vehicle such as bicycles or the like, or in any motor vehicle such as trucks, motorcycles, drag racing cars, or the like, wherein measurement of and reaction to the performance of the vehicle in terms of the grip between its wheels and the road, track, or other surface may be measured and reacted to or otherwise managed.

Figure 1:
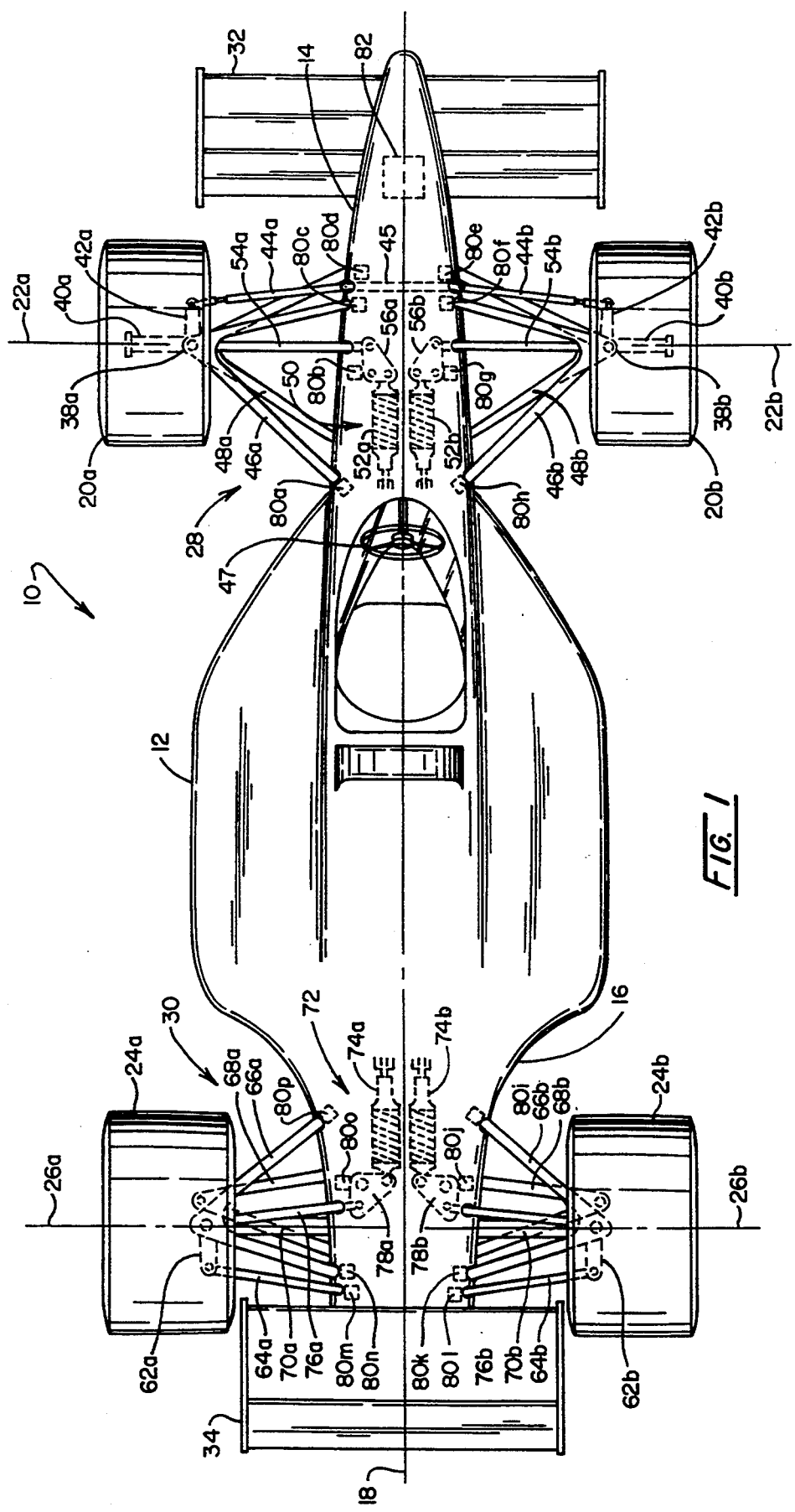
FIG. 1 is a plan view of a representative road racing car showing the symmetry of the car about its longitudinal centerline.

Considering then FIG. 1, a road racing car of the "Indy" or Formula 1 type is depicted generally at 10. Road racing car 10 is seen to comprise a chassis, 12, which extends between a forward portion, 14, and a rearward portion 16, along a longitudinal centerline, 18. For imparting motion to car 10, a pair of front wheels, 20a and 20b, are positioned at forward portion 14 along axial centerlines, 22a and 22b, and a pair of rear wheels, 24a and 24b, are positioned at rearward portion 16 along corresponding axial centerlines, 26a and 26b. Chassis 12 is supported on front wheels 20 by a front suspension system, shown generally at 28, and on rear wheels 24 by a rear suspension, shown generally at 30. Extending from forward portion 14 of chassis 12 is a front wing, 32, and extending from rearward portion 16 is a rear wing, 34. Wings 32 and 34 are positionable to affect the aerodynamics of car 10.

Figure 2:
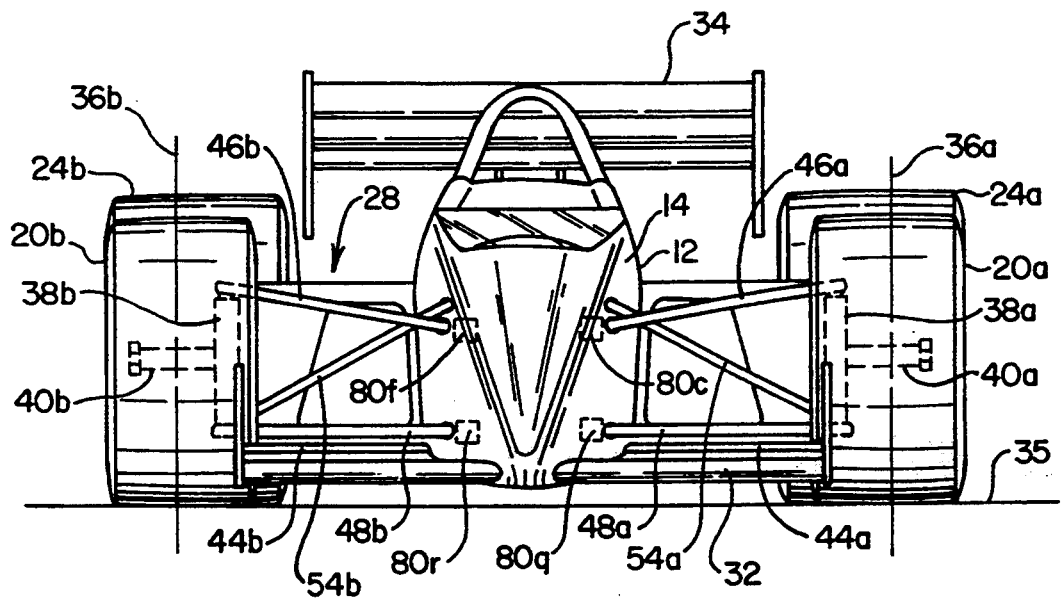
FIG. 2 is a front elevational view of the road racing car of FIG. 1.

Looking additionally to FIG. 2, front wheels 20a and 20b each may be seen to rest on a ground surface which defines a ground plane, 35, and to be positioned, respectively, along a vertical centerline, 36a and 36b. It will be understood that, depending upon the surface geometry of the ground surface defining ground plane 35, ground plane 35 maybe considered to be a single plane or separate planes at each of the wheels 20 and 24 of car 10. Uprights 38a and 38b are provided to support, respectively, wheels 20a and 20b, and are each formed as having, respectively, an axle portion, 40a and 40b, supporting the mounting of wheels 20, and a steering arm portion, 42a and 42b. For controlling the steering position or angle of wheels 20a and 20b, steering arm portions 42a and 42b are pivotally-coupled, respectively, to a steering tie rod, 44a and 44b, each of which extends inwardly to a pivotal coupling with a common steering rack, 45. Steering rack 45, in turn, is coupled to a steering wheel, 47, the rotation thereof controlling the movements of rack 45 and steering tie rods 44 affecting the steering angle position of wheels 20, i.e., the relative angle between the axial centerlines 22 of wheels 20 and the longitudinal centerline 18 of car 10. Uprights 38a and 38b are pivotally-coupled to chassis 12 additionally via a pair of upper A-arms or wishbones, 46 and 46b, and a pair of lower A-arms or wishbones, 48a and 48b, each of which are configured as having a pair of elongate legs meeting at an apex to define a predetermined angle therebetween.

To dampen the shock forces jarring the forward portion 14 of chassis 12 during the motion of car 10, an inboard-mounted shock absorber system, shown generally at 50, is provided as an arrangement of a pair of longitudinally-mounted shock absorbers, 52a and 52b, which may be of the hydraulic or pneumatic-type and which may include a pair of springs. Transferring the shock forces from wheels 20a and 20b are a pair pushrods, 54a and 54b, each of which normally extends along a predetermined angle with respect to vertical centerlines 36 between a first end pivotally-coupled to an upright 38, and a second end pivotally-coupled to a shock absorber 52 via a rocker, 56a and 56b. The pivotal coupling of pushrods 54 to an upright 38 allows for the rotational movement thereof relative to chassis 12.

Figure 3:
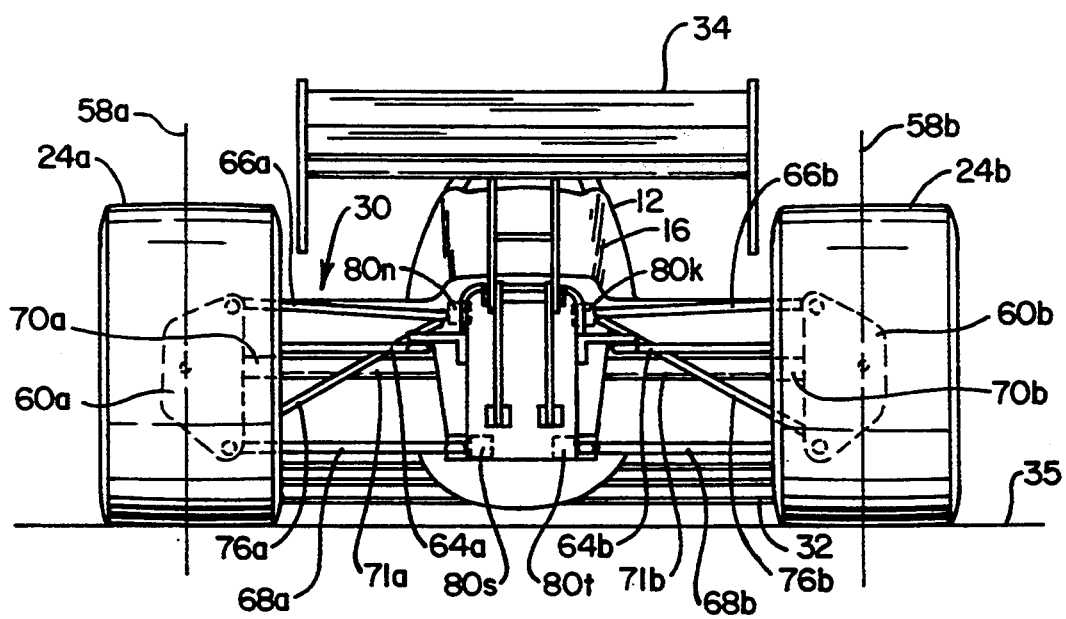
FIG. 3 is a rear elevational view of the road racing car of FIG. 1.

Returning to FIG. 1, and looking additionally to FIG. 3, rear wheels 24a and 24b, resting witch front wheels 20 on ground plane 35, may be seen to be positioned along a corresponding vertical centerline, 58a and 58b, and to be mounted on a corresponding upright, 60a and 60b. Uprights 60a and 60b each are formed as having, respectively, a toe link portion, 62a and 62b, each of which are pivotally-coupled, respectively, to a tie rod, 64a and 64b, each of which extends inwardly to a pivotal coupling with chassis 12. Uprights 60a and 60b are pivotally-coupled to chassis 12 additionally via a pair of upper A-arms or wishbones, 66a and 66b, and a pair of lower A-arms or wishbones, 68a and 68b, each of which are configured as having a pair of elongate legs meeting at an apex to define a predetermined angle therebetween. A pair of axles, 70a and 70b, are pivotally-coupled to chassis 12 via, respectively, shafts 71a and 71b, each of which extends between chassis 12 and an axle. 70 for transmitting drive power to rear wheels 24.

As was provided for forward portion 14, an inboard-mounted shock absorber system, shown generally at 72, is provided in a like manner to dampen the shock forces jarring the rearward portion 16 of chassis 12 during the motion of car 10. In like manner, shock absorber system 72 is provided as an arrangement of a pair of longitudinally-mounted shock absorbers, 74a and 74b, which also may include a pair of springs and be of the hydraulic or pneumatic-type, and which are transferring the shock forces from wheels 24a and 24b via a pair pushrods, 76a and 76b. Pushrods 76a and 76b each normally extends along a predetermined angle with respect to vertical centerlines 58 between a first end pivotally-coupled to an upright 60, and a second end pivotally-coupled to a shock absorber 74 via a rocker, 78a and 78b. Again, the pivotal coupling of pushrods 54 to an upright 38 allows for the rotational movement thereof relative to chassis 12.

Returning to FIG. 1, and looking also to FIGS. 2 and 3, the component members of front suspension 28 and rear suspension 30 each are shown as being equipped with force sensors, 80a–t, for measuring the instantaneous load force vectors acting on each suspension member during the motion of car 10. In accordance with the precepts of the present invention, it has been discovered that the vectors acting on the suspension members directly relate to the frictional grip or roadholding forces within the contact patches between wheels 20 and 24 and ground plane 10. It is these frictional grip forces which have been found herein to be the determining factor in the ultimate performance of vehicles such as car 10 in terms of braking, acceleration, and cornering.

Force sensors 80 may be of the strain gauge or load cell type, and may additionally comprise linear or rotational displacement components for measuring direction for providing load force output signals corresponding to the magnitude and relative direction of those load force vectors. For purposes of illustration, force sensors 80 are shown being positioned between the component members of suspensions 28 and 30 and chassis 12. However, depending upon the design preference of the practitioner, sensors 80 may be positioned directly on the members of suspensions 28 and 30, between the members and uprights 38 and 60, or, and as will be detailed hereinafter, between the bearings of axles 40 and 70 and uprights 38 and 60. Indeed, as the system and method of the invention herein described are, adaptable to a variety of sensor positions, it will be appreciated that the invention herein involved should not be construed as being limited to any particular placement or arrangement of sensors.

For storing and analyzing the load force output signals provided by sensors 80, a processor, as is represented at block 82 of FIG. 1, may be provided on board car 10. Alternatively, the load force output signals provided by sensors 80 simply may be stored in processor 82 for downloading to a personal computer or the like, or may be transmitted through a real-time telemetry linkup to an external station for analysis.

To derive meaningful values from the load force output signals provided by sensors 80, it is necessary to relate the components of each of the load force vectors represented thereby, which vectors may be resolved with respect to any relative plane, to a common reference plane to derive normalized load force components which then may be summed. Preferably, such reference plane is selected to be ground plane 35 such that the normalized component vectors related thereto directly correspond to the lateral load force between ground plane 35 and the wheels 20 and 24 of car 10 which is directed transverse to the longitudinal centerline 18 of car 10, to the longitudinal load force which is directed parallel to longitudinal centerline 18, and to the vertical load force which is directed perpendicular to ground plane 35. In this way, the summed and normalized components of the force vectors taken from the members of suspensions 28 and 30 are made to relate directly to the frictional grip forces with the contact patches between wheels 20 and 24 and ground plane 35, and thereby are directly useful for providing a measurement of the ultimate grip or roadhandling performance of car 10. By grip or roadhandling performance, it is meant the degree to which a cornering force can be developed without the driver losing full control of the car. For maximum roadholding, it is necessary that the wheels of the car be maintained at an angle optimizing the area of the contact patch at the interface between the tire and the road surface.

Figure 4:
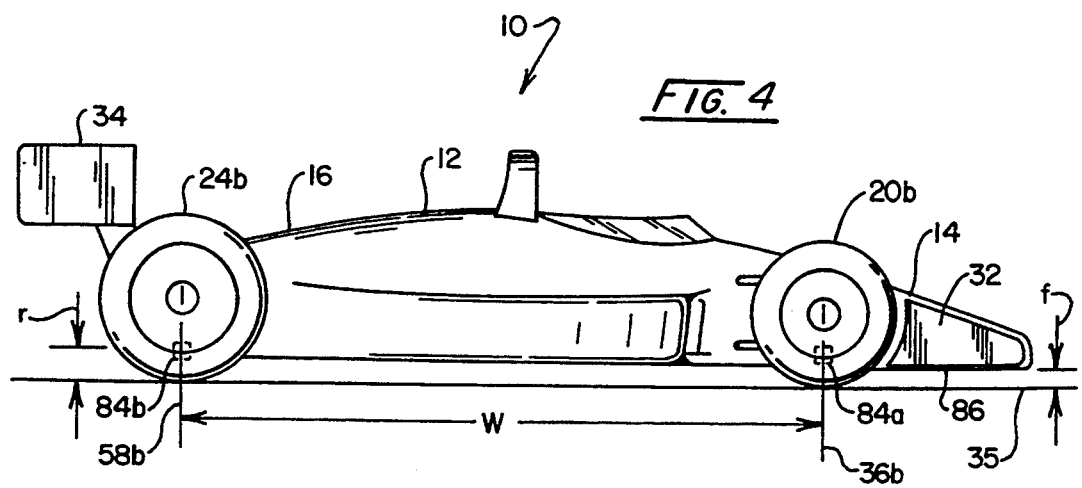
FIG. 4 is a side elevational view of the road racing car of FIG. 1 showing a methodology for measuring the attitude angle between the bottom reference plane of the car and the ground plane.

Looking to FIG. 4, it will be appreciated that in relating the load force vectors represented by the load force output signals of sensors 80 to ground plane 35, the relationship of the component members of, for example, car suspension 30 of car 10 will be affected by the distances between the forward portion 14 and rearward portion 16 of chassis 12 from ground plane 35. In this regard, car 10 may be provided as having at least a pair of distance sensors, 84a and 84b, which may be of a laser or a sonic-type and which may be mounted as is shown at a first forward point and a second rearward point along chassis 12. Mounted as illustrated, sensors 84a and 84b will be seen to derive distance output signals corresponding to the distances, designated respectively by "f" and "r", at vertical centerlines 36b and 58b measured between ground plane 35 and the lower surface of chassis 12 defining a bottom plane, 86, of car 10. Accordingly, an attitude angle, $\theta$, may be derived according to expression:

$$\theta = \tan^{-1}((r-f)/w) \tag{1}$$

where "w" is wheelbase length between vertical centerlines 36b and 58b. Attitude angle $\theta$ then may be related to the components of the load force vectors to derive components normalized to ground plane 35. It may be noted, however, if the measurement of angle $\theta$ is desired to be effected with somewhat more accuracy, then distance "f" may be measured from a more rearward location, with the length "w" being scaled accordingly. Indeed, angle $\theta$ may be measured as between any two forward and rearward points along chassis 12, or alternatively, directly from distance sensors mounted on each upright 38 or 60. Measuring angle $\theta$ directly off each upright 39 or 60 will be understood to provide separate readings for relation of each wheel 20 and 24 to a separate ground plane 35.

Figure 5:
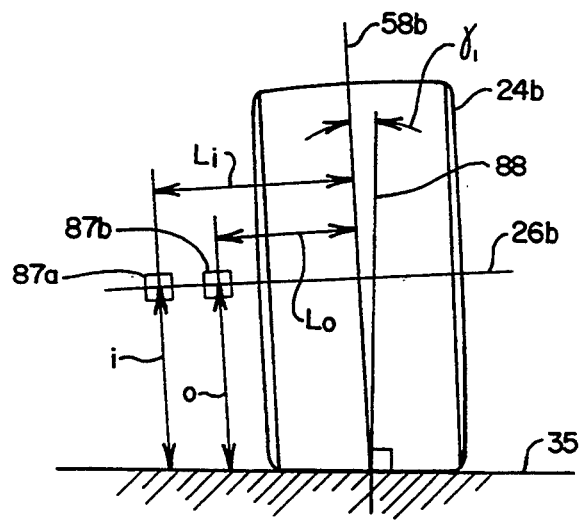
FIG. 5 is a schematic representation of a wheel of the road racing car of FIG. 1 showing a methodology for measuring the camber angle between the vertical centerline of the wheel and a line directed perpendicular to the ground plane.

Turning to FIG. 5, wherein a wheel of car 10 (FIGS. 1-3) is shown in schematic form as rear wheel 24b, it will be appreciated that the relationship of the component members of suspension 30, for example, to ground plane 35 additionally will be affected by the distance between the vertical centerline 58b of wheel 24b and the ground plane 35. Accordingly, at least a pair additional distance sensors, represented at 87a and 87b, may be mounted, for example, on the upright 60b (FIG. 3) of rear wheel 24b, for providing distance output signals at two points along axial centerline 26b corresponding to the distances represented by the designations "i" and "o". In this way, and with the distances designated by "$L_i$" and "$L_o$" being known parameters, an instantaneous camber angle, T, may be derived between vertical centerline 58b of wheel 24b and line 88 directed perpendicular to ground plane 35 according to expression:

$$\gamma = \tan^{-1}((o-i)/(L_i-L_o)) \tag{2}$$

As was attitude angle $\theta$, camber angle $\gamma$ then may be used for relation with the components of the load force vectors represented by the load force output signals of sensors 80 to derive component vectors which are normalized to ground plane 35.

Figure 6:
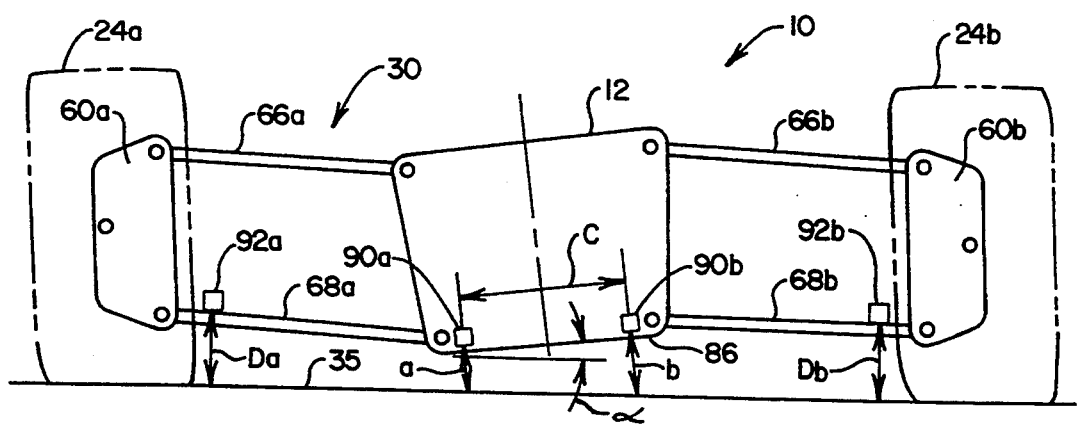
FIG. 6 is a schematic representation of a wheel pair and supporting suspension of the racing car of FIG. 1 showing a methodology for measuring the roll angle between the bottom reference plane of the car and the ground plane.

Looking to FIG. 6, wherein a wheel pair of car 10 is exemplified by rear wheels 24 and rear suspension 30 as depicted in a block schematic form, it will be realized that the relationship of the members forming, for example, suspension 30 to ground plane 35 and to chassis 12 will be affected during cornering and the like by the roll angle of chassis 12. For measuring this roll angle, at least a pair of additional distance sensors, 90a and 90b, may be mounted at two points on chassis 12 generally transverse to longitudinal centerline 18 (FIG. 1). So mounted, sensors 90a and 90b may derive distance output signals corresponding to the distances designated respectively by "a" and "b", allowing for the calculation of a roll angle, $\alpha$, between bottom plane 86 of chassis 12 and ground plane 35 according to the expression:

$$\alpha = \tan^{-1}((b-a)/c) \tag{3}$$

where "c" is the distance between sensors 90a and 90b. As were attitude angle $\theta$ and camber angle $\gamma$, roll angle $\alpha$ then may be used for relation with the components of the load force vectors represented by the load force output signals of sensors 80 to derive component vectors which are normalized to ground plane 35.

As an alternative or in addition to the foregoing methodologies for determining attitude angle $\theta$, camber angle %, and roll angle a, distance measurements to ground plane may be taken directly from the component members forming suspensions 28 and 30. As is shown in FIG. 6 for rear suspension 30, outboard distance sensors, as are represented at 92a and 92b, may be mount on lower A-arms 68, for example, for deriving distance output signals corresponding to the distance between A-arms 68 and ground plane 35. Such output signals then may be used for relation with the components of the load force vectors corresponding to the load force output signals of sensors 80 to derive component vectors which are normalized to ground plane 35.

Figure 7:
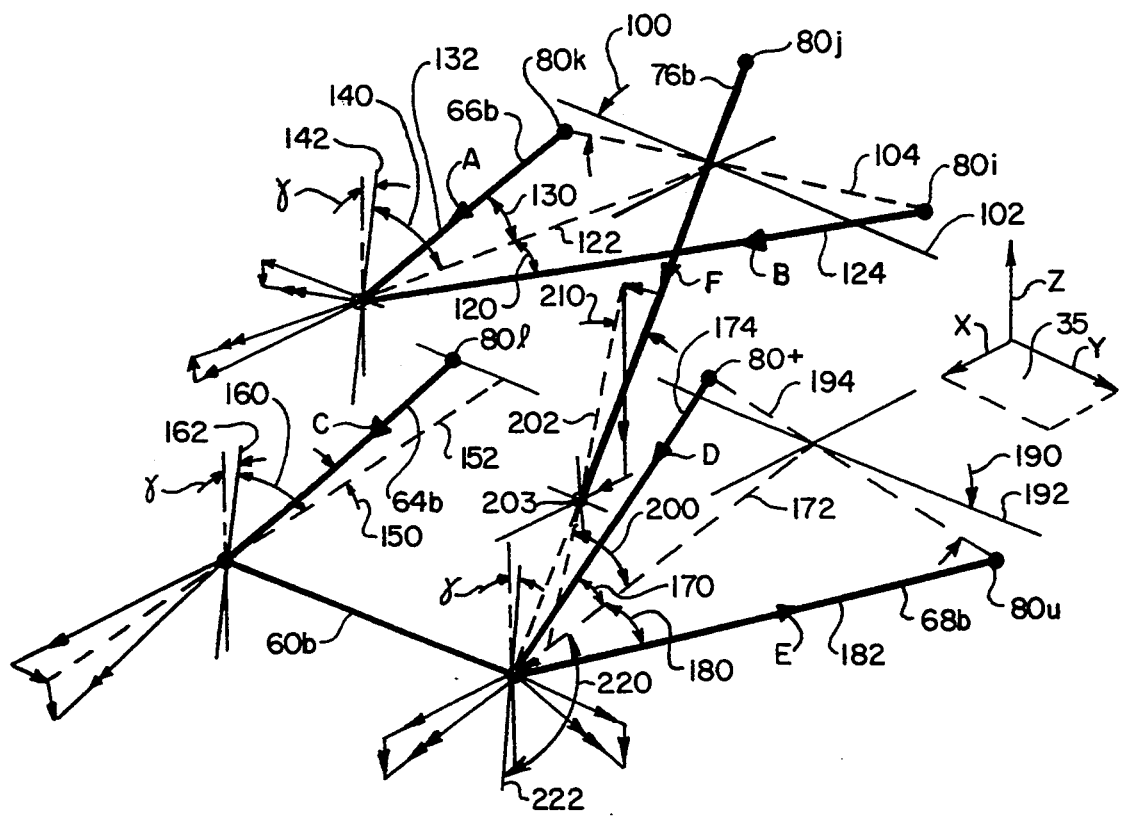
FIG. 7 is a free body diagram of the force vectors developed in the suspension elements of a rear wheel of the road racing car of FIG. 1.

As illustrative of the application of the foregoing system and method to the measurement of the grip forces at the wheels of a road racing car such as car 10, rear wheel b and its supporting suspension members, namely, upright 60b, tie rod 64b, upper A-arm 66b, lower A-arm 68b, and pushrod 76b, are considered in terms of the free body diagram depicted in FIG. 7. In FIG. 7, force sensors 80 from FIGS. 1 and 3, which provide load force output signals corresponding to the load force vectors acting on the suspension members, are commonly referenced at 80i, 80j, 80k, 80l, and 80t, with force sensor 80u additionally being shown. To facilitate the resolution of the force vectors measured by sensors 80 and their relation to a common reference plane such as ground plane 35, reference may be made to the coordinate axes shown at x, y, and z which are directed, respectively, transverse to the longitudinal centerline 18 of car 10, parallel to longitudinal centerline 18, and perpendicular to ground plane 35. Further, definition of the following values, with reference to coordinate axes x and y, defining horizontal directions, and z, defining a vertical direction, is helpful:

TABLE 2

Angle 100 between the horizontal plane represented by line 102, and the line represented at 104 joining the inboard centers of upper A-arm 66b;

Angle 120 between the transverse vertical plane, represented by line 122, through the outboard center of upper A-arm 66b, and the front leg 124 thereof;

Angle 130 between the transverse vertical plane, represented by line 122, through the outboard center of upper A-arm 66b, and the rear leg 132 thereof;

Angle 140 between upright plane, represented by line 142, parallel to the center of wheel 24b, and the transverse vertical plane, represented by line 122, through the outboard center of upper A-arm 66b;

Angle 150 between tie rod 64b and the transverse vertical plane, represented by line 152, through the outboard center of tie rod 64b;

Angle 160 between the upright plane, represented by line 162, parallel to the center of wheel 24b, and the transverse vertical plane, represented by line 152, through the outboard center of tie rod 64b;

Angle 170, between the transverse vertical plane, represented by line 172, through the outboard center of lower A-arm 68b, and the rear leg 174 thereof;

Angle 180 between the transverse vertical plane, represented by line 172, through the outboard center of lower A-arm 68b, and the front leg 182 thereof;

TABLE 2-continued

Angle 190 between the horizontal plane represented by line 192, and the line represented at 194 joining the inboard centers of lower A-arm 68b;

Angle 200 between the lower A-arm plane defined by line 194 and legs 174 and 182 of lower A-arm 68b, and the intersection of the pushrod plane defined by line 202 and pushrod 76b, and a transverse vertical plane through the outboard center 203 of pushrod 76b;

Angle 210 between pushrod 76b and the transverse vertical plane, represented by line 202, through the outboard center 203 of pushrod 76b;

Angle 220 between upright plane, represented by line 222, parallel to the center of wheel 24b, and the transverse vertical plane, represented by line 172, through the outboard center of lower A-arm 68b;

Attitude angle $\theta$ between ground plane 35 and bottom plane 86 of car 10;

Camber angle $\gamma$ of rear wheel 24b relative to ground plane 35;
Force A in rear leg 132 of upper A-arm 66b;
Force B in front leg 124 of upper A-arm 66b;
Force C in tie rod 64b;
Force D in rear leg 174 of lower A-arm 68b;
Force E in front leg 182 of lower A-arm 68b; and
Force F in pushrod 76b.

It also may be assumed for purposes of illustration that the inboard mount centers of upper A-arm 66b are spaced equidistant from a central vertical plane of car 10 extending through its longitudinal centerline 18, and that the inboard mount centers of lower A-arm 68b similarly are spaced equidistant from that central vertical plane. From the distance measuring methodologies described hereinbefore, angles $\theta$, $\gamma$, and $\alpha$ may determined. The analysis then may proceed to a consideration of the forces acting on upper A-arm 66b as follows, wherein all numbers relate to reference numerals rather than to numerical quantifies except where noted:

(a) Lateral load force in relative plane of upper A-arm 66b:
$$A \cos 130 + B \cos 120 \quad (4)$$
(b) Lateral load force of upper A-arm 66b normalized to ground plane 35:
$$(A \cos 130 + B \cos 120) \cos(\gamma + 140 - 90°) \quad (5)$$
(c) First normalized vertical load force component derived from normalized lateral load force:
$$(A \cos 130 + B \cos 120) \sin(\gamma + 140 - 90°) \quad (6)$$
(d) Longitudinal load force in relative plane of upper A-arm 66b:
$$A \sin 130 - B \sin 120 \quad (7)$$
(e) Longitudinal load force normalized to ground plane 35:
$$(A \sin 130 - B \sin 120) \cos(100 - \theta) \quad (8)$$
(f) Second normalized vertical load force component derived from normalized longitudinal load force:
$$(A \sin 130 - B \sin 120) \sin(100 - \theta) \quad (9)$$
(g) Total normalized vertical load force component:
$$(A \cos 130 + B \cos 120)(\sin(\gamma + 140 - 90°)$$
$$+ (A \sin 130 - B \sin 120) \sin(100 - \theta) \quad (10)$$

Considering next the forces acting on lower A-arm 68b as follows:
(a) Lateral load force in relative plane of bottom A-arm 68b:
$$D \cos 170 - E \cos 180 \quad (11)$$
(b) Lateral load force of lower A-arm 68b normalized to ground plane:
$$(D \cos 170 - E \cos 180) \sin(220 - \gamma) \quad (12)$$
(c) First normalized vertical load force component derived from normalized lateral load force:
$$- (D \cos 170 - E \cos 180) \cos(220 - \gamma) \quad (13)$$
(d) Longitudinal load force in relative plane of lower A-arm 68b:
$$D \sin 170 + E \sin 180 \quad (14)$$
(e) Longitudinal load force normalized to ground plane 35:
$$(D \sin 170 + E \sin 180) \cos(190 + \theta) \quad (15)$$
(f) Second normalized vertical load force component derived from normalized longitudinal load force:
$$- (D \sin 170 + E \sin 180) \sin(190 + \theta) \quad (16)$$
(g) Total normalized vertical load force component:
$$- (D \cos 170 - E \cos 180) \cos(220 - \gamma)$$
$$- (D \sin 170 + E \sin 180) \sin(190 + \theta) \quad (17)$$

Continuing with an analysis of the forces acting on tie rod 64b:
(a) Lateral load force in relative plane of tie rod 64b:
$$C \cos 150 \quad (18)$$
(b) Lateral load force normalized to ground plane 35:
$$C \cos 150 (\cos(160 + \gamma - 90°)) \quad (19)$$
(c) Normalized vertical force component derived from normalized lateral load force:
$$- C \cos 150 (\sin(160 + \gamma - 90°)) \quad (20)$$
(d) Longitudinal load force component relative to ground plane 35:
$$C \sin 150 \quad (21)$$

Finishing with an analysis of the pushrod force components:
(a) Longitudinal force from pushrod:
$$- F \sin 210 \quad (22)$$
(b) Pushrod vertical force:
$$- F \sin 210 (\sin(200 - \gamma + 220 - 90°)) \quad (23)$$
(c) Pushrod lateral force:
$$F \cos 210 (\cos(200 - \gamma + 220 - 90°)) \quad (24)$$

From Eqs. 4-24, an instantaneous total force balance on suspension members 60b, 64b, 66b, 68b, and 76b supporting wheel 24b may be determined and normalized with respect to ground plane 35. The components of the instantaneous grip forces within the contact patch at the interface of wheel 24b and ground plane 35 therefore are as follows:

(a) Total vertical load force directed normal to ground plane 35:
$$(A \cos 130 + B \cos 120) \sin(\gamma + 140 - 90°) +$$
$$(A \sin 130 - B \sin 120)$$
$$* \sin(100 - \theta) - ((D \cos 170 - E \cos 180)$$
$$\cos(220 - \gamma))$$
$$- (D \sin 170 + E \sin 180) \sin(190 + \theta) - C$$
$$\cos 150 \sin(160 + \gamma - 90°)$$
$$- F \sin 210 (\sin(200 - \gamma + 220 - 90°)) \quad (25)$$
(b) Total lateral load force directed within ground plane 35 transverse to longitudinal centerline 18 of car 10:
$$(A \cos 130 + B \cos 120) \cos(\gamma + 140 - 90°) +$$
$$(D \cos 170 - E \cos 180) \sin(220 - \gamma)$$
$$+ C \cos 150 (\cos(160 + \gamma - 90°)) + F \cos 210$$
$$* (\cos(200 - \gamma + 220 - 90°)) \quad (26)$$
(c) Total longitudinal load force directed within ground plane 35 parallel to longitudinal centerline 18 of car 10:
$$(A \sin 130 - B \sin 120) \cos(100 - \theta) +$$
$$(D \sin 170 + E \sin 180)$$
$$* \cos(190 + \theta) + C \sin 150 - F \sin 210 \quad (27)$$

Although the load forces given by Eqs. 25-27 may be used directly, for example, as objective criteria upon which may be assessed the comparative grip performance of car 10, a total force balance on wheel 24b also may be derived therefrom. In this regard, contributions which must be considered to complete the force balance include the lateral centripetal forces developed during cornering, as well as longitudinal lift and vertical and lateral drag aerodynamic forces acting on the surfaces of wheel 24b.

Figure 8:
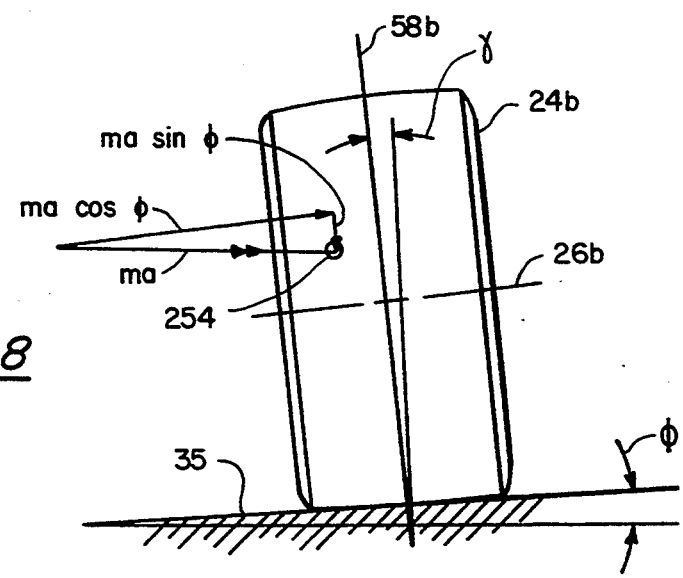
FIG. 8 is a schematic representation of the relationship between a wheel of the car of FIG. 1 and the ground plane.
Figure 9:
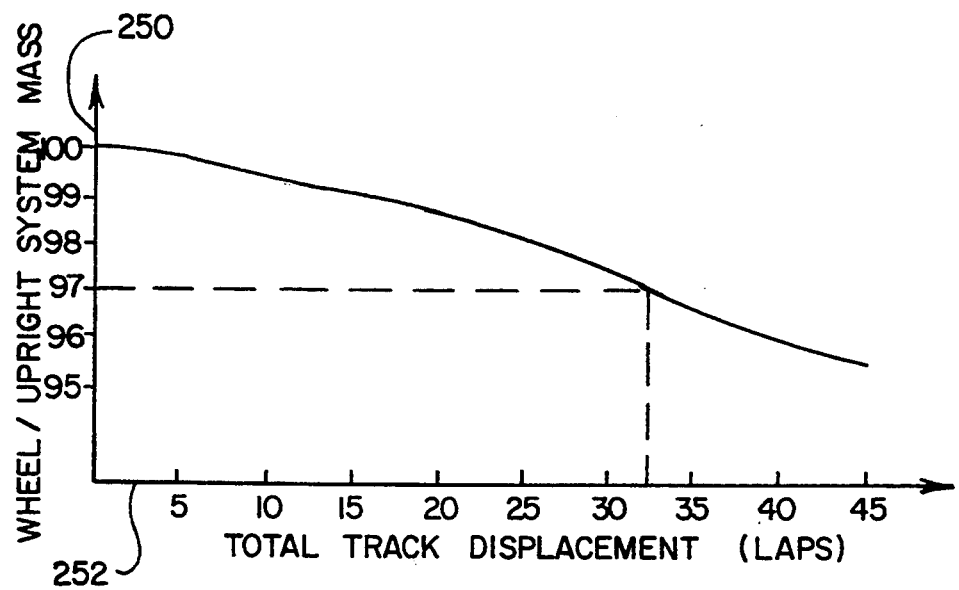
FIG. 9 is a graphical representation of the change in mass of the wheel and upright system of FIG. 8 as a function of lap number.

Considering firstly the influence of centripetal force, and looking to FIG. 8 which is schematic depiction of the relationship between wheel 24b and ground plane 35 which is represented as a banked-oval track, from an established graph of track banking angle, $\phi$ versus track position, the banking angle $\phi$ of the track may be determined for any instantaneous position of car 10. Further, the mass, m, of the system comprising wheel 24b and upright 60b may be assumed constant, or, as is shown in FIG. 9, may be calculated to account for rubber and brake pad losses from an established graph of system mass, 250, versus track displacement or lap number, 252. Additionally, the lateral acceleration, $a$, of car 10 directed transverse to its longitudinal centerline 18 may be continually monitored with sensors which may be, for example, of the accelerometer-type. As is shown in FIG. 8 with reference to the center of mass, 254, of wheel 24b and upright 60, with m, $a$, and $\phi$ being defined values, the lateral and vertical components of the centripetal force on wheel 24b may be determined as follows:

| | |
|---|---|
| Centrifugal vertical force on wheel 24b: | |
| ma sin $\phi$ | (28) |
| Centrifugal lateral force on wheel 24b: | |
| ma cos $\phi$ | (29) |

Figure 10:
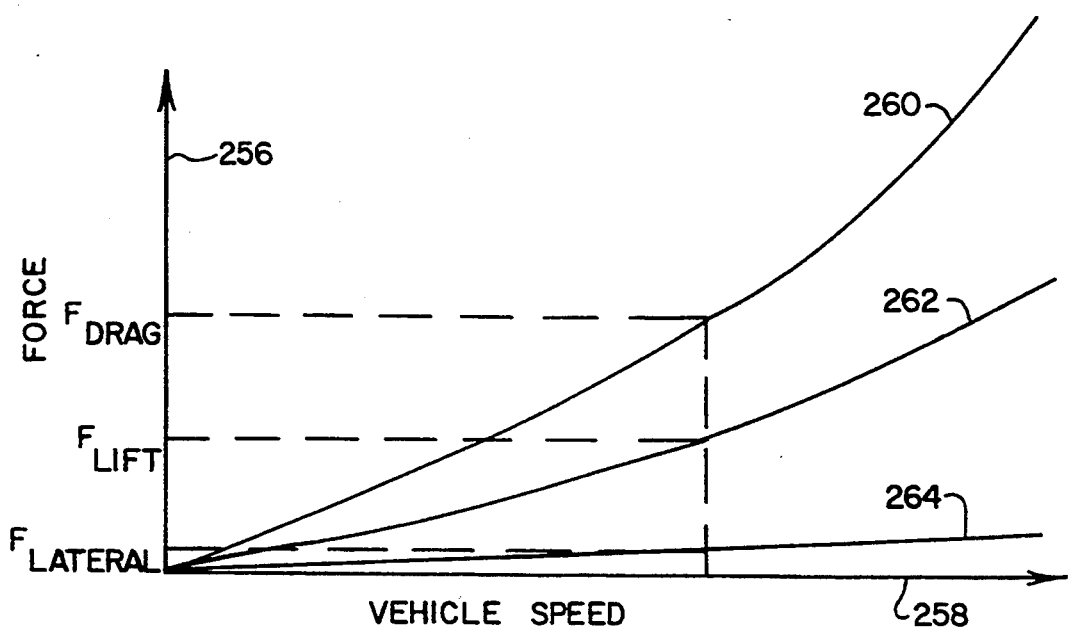
FIG. 10 is a graphical representation of the aerodynamic drag, lift, and lateral forces acting on the wheel of FIG. 8 as functions of car speed.

Considering secondly the influence aerodynamic forces acting on wheel 24b, reference is made to FIG. 10 which is a plot of the aerodynamic forces, 256, acting on wheel 24b as functions of the speed of car 10, 258. If the speed of car 10 is known, then the aerodynamic lift, lateral, and drag force on wheel 24b may be measured for a given aerodynamic environment and toe and camber setting. From these measurements, the instantaneous drag, 260, lift, 262, and lateral, 264, forces may be determined from established[graphs such as those depicted in FIG. 10. With the centripetal, aerodynamic, and load forces on wheel 24b being determined as illustrated, a total force balance may be evolved.

Figure 11:
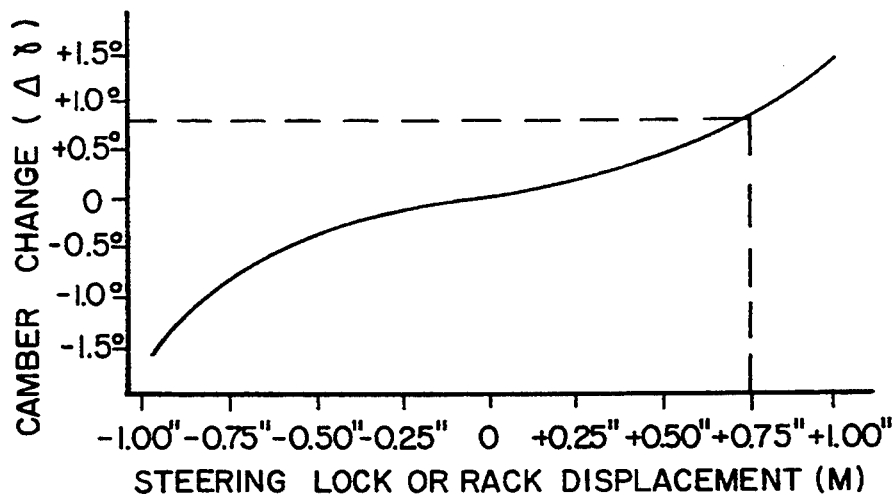
FIG. 11 is a graphical representation of the change in the camber angle of FIG. 5 as a function of the linear displacement of the steering rack of the road racing car of FIG. 1.

Continuing with the illustrative of the application of the inventive system and method to the measurement of the grip forces at the wheels of a car 10, next considered is front wheel 20b. As before, angles $\theta$, $\gamma$, and $a$ may be defined as was detailed, respectively, in connection with FIGS. 4, 5, and 6. Additionally, as is shown in connection with FIG. 11, it is helpful for wheels such as front wheels 20 which are not fixed relative, to chassis 12, to measure the change in camber angle $\gamma$ as a function of the linear displacement of steering rack 45. Through reference to an established graph such as that depicted in FIG. 11 defining a camber change, $\Delta\gamma$, as a function of steering lock or rack 45 displacement, M. From a graph such as that shown in FIG. 11, for a given displacement M of steering rack 45, the corresponding camber change $\Delta\gamma$ may be determined for relation to the measured camber angle $\gamma$.

Figure 12:
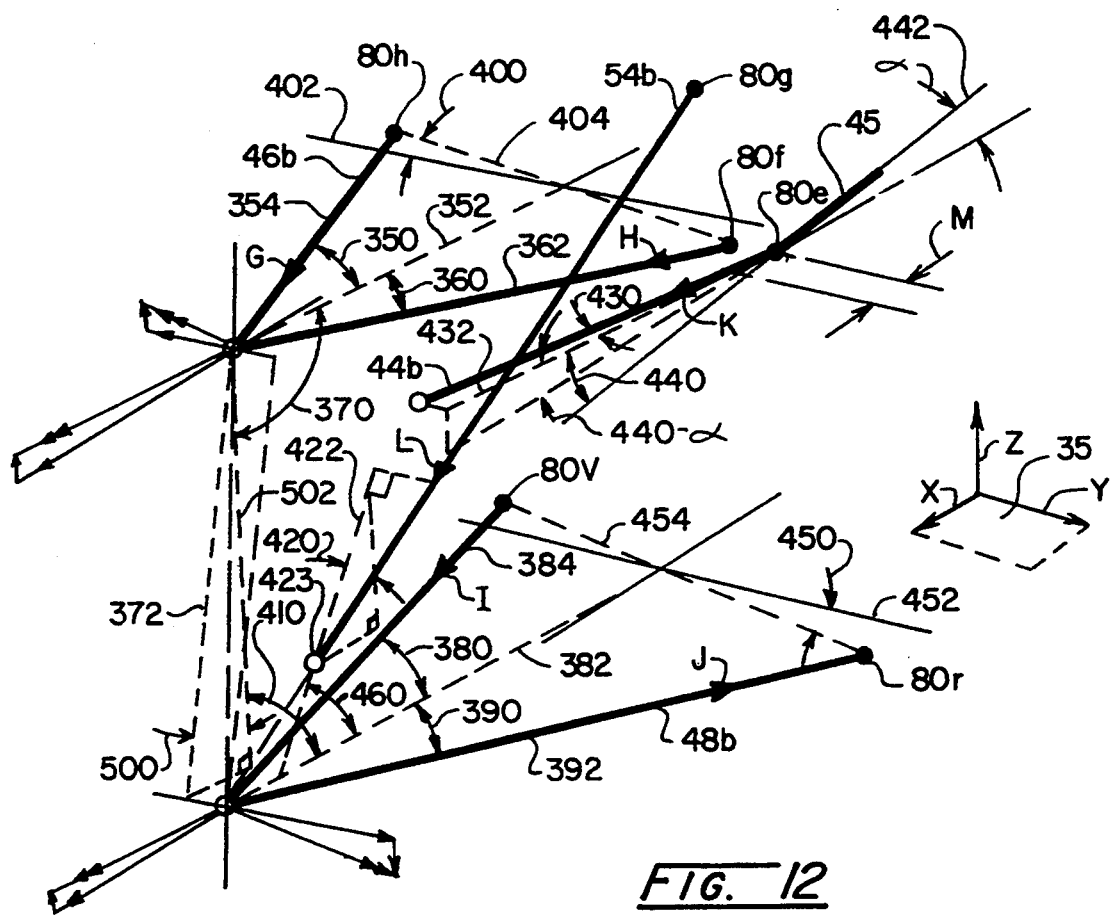
FIG. 12 is a free body diagram of the force vectors developed in the suspension elements of a front wheel of the road racing car of FIG. 1.

Turning now to FIG. 12, front wheel 20b and its supporting suspension members, namely, upright 38b, steering tie rod 44b, steering rack 45, upper A-ann 46b, lower A-ann 48b, and pushrod 54b are shown in terms of a free body diagram. Also shown are force sensors 80 from FIGS. 1 and 3, which provide load force output signals corresponding to the load force vectors acting on the suspension members, are commonly referenced at 80e, 80f, 80g, 80g, 80h, and 80r, with force sensor 80v additionally being shown. Again, to facilitate the resolution of the force vectors measured by sensors 80 and their relation to a common reference plane such as ground plane 35, reference may be made to the coordinate axes shown at x, y, and z which are directed, respectively, transverse to the longitudinal centerline 18 of car 10, parallel to longitudinal centerline 18, and perpendicular to ground plane 35. Further, definition of the following values, with reference to coordinate axes! x, y, and z, is helpful:

TABLE 3

Angle 350 between the transverse vertical plane, represented by line 352, through the outboard center of upper A-arm 46b, and the rear leg 354 thereof;

Angle 360 between the transverse vertical plane, represented by line 352, through the outboard center of upper A-arm 46b, and the front leg 362 thereof;

Angle 370 between the kingpin line represent at 372 and the transverse vertical plane, represented by line 352, through the outboard center of upper A-arm 46b;

Angle 380 between the transverse vertical plane, represented by line 382, through the outboard center of lower A-arm 48b, and the rear leg 384 thereof;

Angle 390 between the transverse vertical plane, represented by line 382, through the outboard center of lower A-arm 48b, and the front leg 392 thereof;

Angle 400 between the horizontal plane represented by line 402, and the line represented at 404 joining the inboard centers of upper A-arm 46b;

Angle 410 between the kingpin line represented at 372, and the transverse vertical plane, represented by line 382, through the outboard center of lower A-arm 48b;

Angle 420 between pushrod 54b, and the transverse vertical plane, represented by line 422, through the outboard center 423 of pushrod 54b;

Angle 430 between steering tie rod 44b, and the transverse vertical plane, represented by line 432, through the inboard center of steering tie rod 44b;

Angle 440 between steering rack 45, and the transverse vertical plane, represented by line 432, through the inboard center of steering tie rod 44b;

Angle 450 between the horizontal plane represented by line 452, and the line represented at 454 joining the inboard centers of lower A-arm 48b;

Angle 460 between the lower A-arm plane defined by line 454 and legs 384 and 392 of lower A-arm 48b, and the intersection of the pushrod plane defined by line 422 and pushrod 54b, and a transverse vertical plane through the outboard center 423 of pushrod 54b;

Angle 500 for a steering rack displacement M equal to 0, between the kingpin line projection onto the transverse vertical plane represented by line 372, and the plane, represented by line 502, through the center of wheel 24b;

Attitude angle $\theta$ between ground plane 35 and bottom plane 86 of car 10;

Camber angle $\gamma$ of front wheel 22b relative to ground plane 35;

Roll angle $a$ between ground plane 35 and bottom plane 86 of car 10;

Steering rack displacement M of steering rack 45;

Camber change $\Delta\gamma$ for a given steeling rack displacement M;

Force G in rear leg 354 of upper A-arm 46b;

Force H in front leg 362 of upper A-arm 46b;

Force I in rear leg 384 of lower A-arm 48b;

Force J in front leg 392 of lower A-arm 48b;

Force K in steering tie rod 44b; and

Force L in pushrod 54b.

It also may be assumed that the inboard mount centers of upper A-arm 46b are spaced equidistant from a central vertical plane of car 10 extending through its longitudinal centerline 18, and that the inboard mount centers of lower A-arm 48b similarly are spaced equidistant from that central vertical plane.

As mentioned, angles 0, T, and $a$ may be determined as explained in connection with FIGS. 4, 5, and 6. Additionally, camber change $A_T$ for a given steering rack displacement M may be determined as explained in connection with FIG. 11 for relation to the camber angle 7 measured at a displacement M equal to 0. With angles $\theta$, $\gamma$, and $a$ thus defined, the analysis then may proceed to a consideration of the forces acting on upper A-arm 46b as follows, wherein all numbers relate to reference numerals rather than to numerical quantifies except where noted:

(a) Lateral load force in relative plane of upper A-arm 46b:

-continued

G cos 350 + H cos 360   (30)

(b) Lateral load force of upper A-arm 46b normalized to ground plane 35:
(G cos 350 + H cos 360)
cos(90° − 370 + γ − Δγ + 500)   (31)

(c) First normalized vertical load force component derived from normalized lateral load force:
(G cos 350 + H cos 360)
sin(90° − 370 + γ − Δγ + 500)   (32)

(d) Longitudinal load force in relative plane of upper A-arm 46b:
G sin 350 − H sin 360   (33)

(e) Longitudinal load force normalized to ground plane 35:
(G sin 350 − H sin 360) cos(400 + θ)   (34)

(f) Second normalized vertical load force component derived from normalized longitudinal load force:
(G sin 350 − H sin 360) sin(400 + θ)   (35)

(g) Total normalized vertical load force component:
(G cos 350 + H cos 360)
sin(90° − 370 + γ − Δγ + 500)
+ (G sin 350 − H sin 360) sin(400 + θ)   (36)

Considering next the forces acting on lower A-arm 48b as follows:

(a) Lateral load force in relative plane of bottom A-arm 48b:
I cos 380 − J cos 390   (37)

(b) Lateral load force of lower A-arm 48b normalized to ground plane:
(I cos 380 − J cos 390)
cos(410 + 500 + γ − Δγ − 90°)   (38)

(c) First normalized vertical load force component derived from normalized lateral load force:
(I cos 380 − J cos 390)
sin(410 + 500 + γ − Δγ − 90°)   (39)

(d) Longitudinal load force in relative plane of lower A-arm 48b:
I sin 380 + J sin 390   (40)

(e) Longitudinal load force normalized to ground plane 35:
(I sin 380 + J sin 390) cos(450+ θ)   (41)

(f) Second normalized vertical load force component derived from normalized longitudinal load force:
(I sin 380 + J sin 390) sin(450+ θ)   (42)

(g) Total normalized vertical load force component:
(I cos 380 − J cos 390)
sin(410 + 500 + γ − Δγ − 90°)
+ (I sin 380 + J sin 390) sin(450+ θ)   (43)

Continuing with an analysis of the forces acting on tie rod 64b:

(a) Lateral load force in relative plane of tie rod 44b:
K cos 430   (44)

(b) Lateral load force normalized to ground plane 35:
K cos 430 (cos(440 − α))   (45)

(c) Normalized vertical force component derived from normalized lateral load force:
K cos 430 (sin(440 − α))   (46)

(d) Longitudinal load force component relative to ground plane 35:
− K sin 430   (47)

Finishing with an analysis of the pushrod force components:
(a) Longitudinal force from pushrod:
− L sin 420   (48)

(b) Pushrod vertical force:
− L cos 420
(sin(460 − 410 − 500 − γ + Δγ+90°))   (49)

(c) Pushrod lateral force:
− L cos 420
(cos(460 − 410 − 500 − γ + Δγ+90°))   (50)

From Eqs. 30–50, an instantaneous total force balance on suspension members 38b, 44b, 45, 46b, 48b, and 54b supporting wheel 20b may be determined and normalized with respect to ground plane 35. The components of the instantaneous grip forces within the contact patch at the interface of wheel 20b and ground plane 35 therefore are as follows:

(a) Total vertical load force directed normal to ground plane 35:

(G cos 350 + H cos 360)

sin(90°− 370 + γ − Δγ + 500)
+ (G sin350 − H sin 360) sin(400 +θ)
+ (I cos 380 − J cos 390)
sin(410 + 500 + γ − Δγ − 90°)
+ (I sin 380 + J sin 390)
sin(450+ θ) + K cos 430 (sin(440 − α))
− L cos 420
(sin(460 − 410 − 500 − γ +Δγ+90°)   (51)

(b) Total lateral load force directed within ground plane 35 transverse to longitudinal centerline 18 of car 10:
(G cos 350 + H cos 360)
cos(90° − 370 + γ − Δγ + 500)
+ (I cos 380 − J cos 390)
cos(410 + 500 + γ − Δγ − 90°)
+ K cos 430 (cos(440 − α)) − L cos
420 (cos(460 − 410 − 500 − γ + Δγ+90°)   (52)

(c) Total longitudinal load force directed within ground plane 35 parallel to longitudinal centerline 18 of car 10:
G sin350 − H sin 360) cos(400 + θ)
+ (I sin 380 + J sin 390) cos(450+ θ)
− K sin 430 − L sin 420   (53)

As before, the load forces represented by Eqs. 51–53 may be used directly as objective criteria, or in deriving a total force balance which includes the influences of the centripetal and aerodynamic forces acting on wheel 24. Further, the foregoing analysis may continue for each of the remaining wheels 20 and 24 of car 10 for completing the overall grip performance characterization of car 10.

Turning to FIGS. 13 and 14, the analysis set forth in Eqs. 4–98 is shown in block diagrammatic form first for rear wheel 24b, FIGS. 13A–G, and then for front wheel 20b, FIGS. 14A–E. In view of diagrams 13 and 14, it will be appreciated that the operations and input/output relationships shown therein are amenable for translation into a machine readable firmware or software program which may be executed by the processor of a personal computer or the like. Looking then to FIG. 13A, a diagram for the operations detailed in Eqs. 4–27 are shown in block schematic form generally at 600. Looking firstly to FIG. 13A, it is seen that input parameters or sensor reading inputs are received at blocks 602, 604, 606, 608, 610, 612, and 614 as, respectively, the values or readings designated, "w", "r", "f", "$L_o$", "i", "o", and "$L_i$". In turn, block 620 receives inputs "w", "r", and "f" for determining attitude angle θ, and block 622 receives inputs "$L_o$", "i", "o", and "$L_i$" for determining camber angle γ.

Figure 13A:
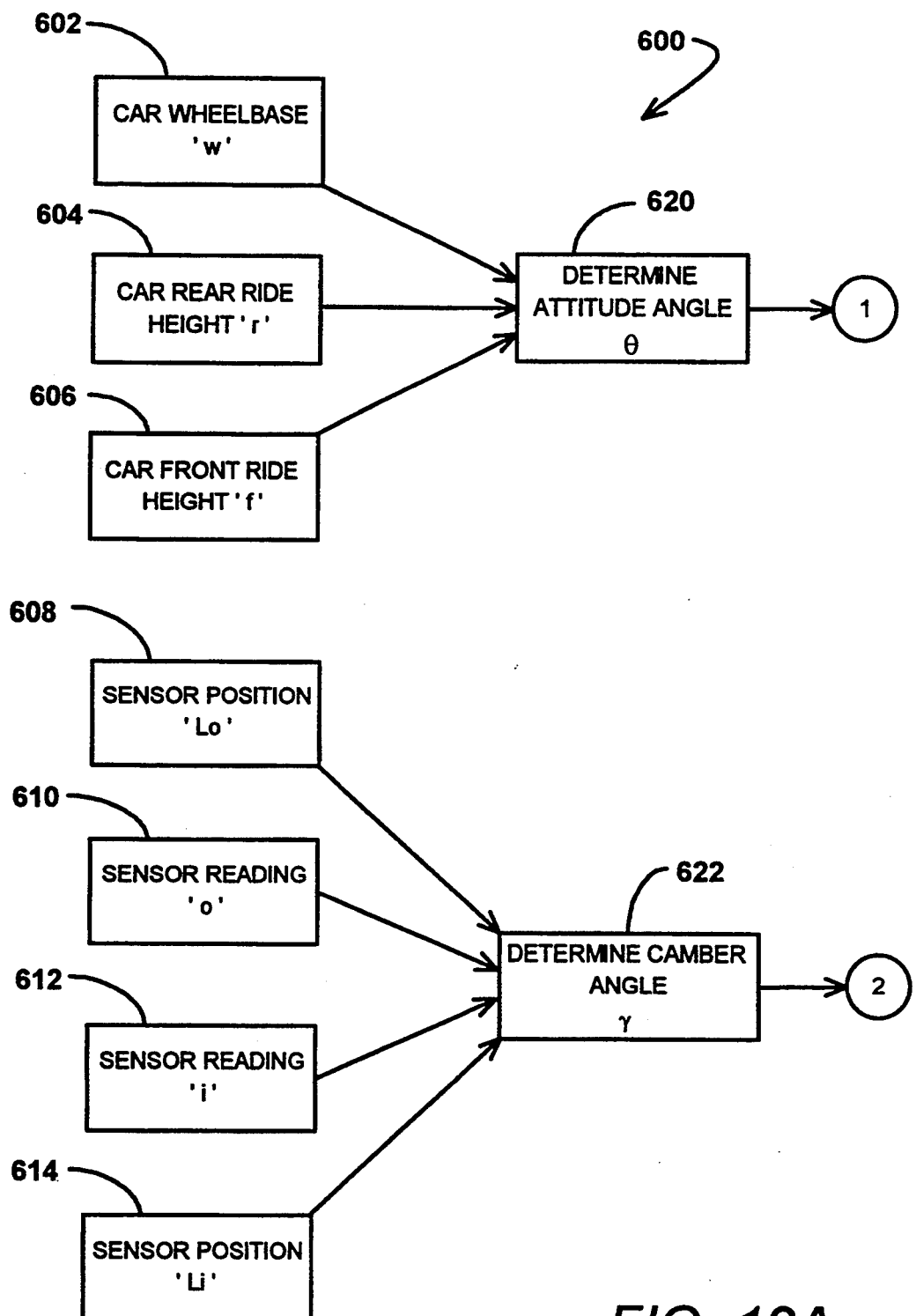
FIGS. 13A–E show a block schematic diagram of a representative arrangement of operations for analyzing the forces shown in the free body diagram of FIG. 7.
Figure 13B:
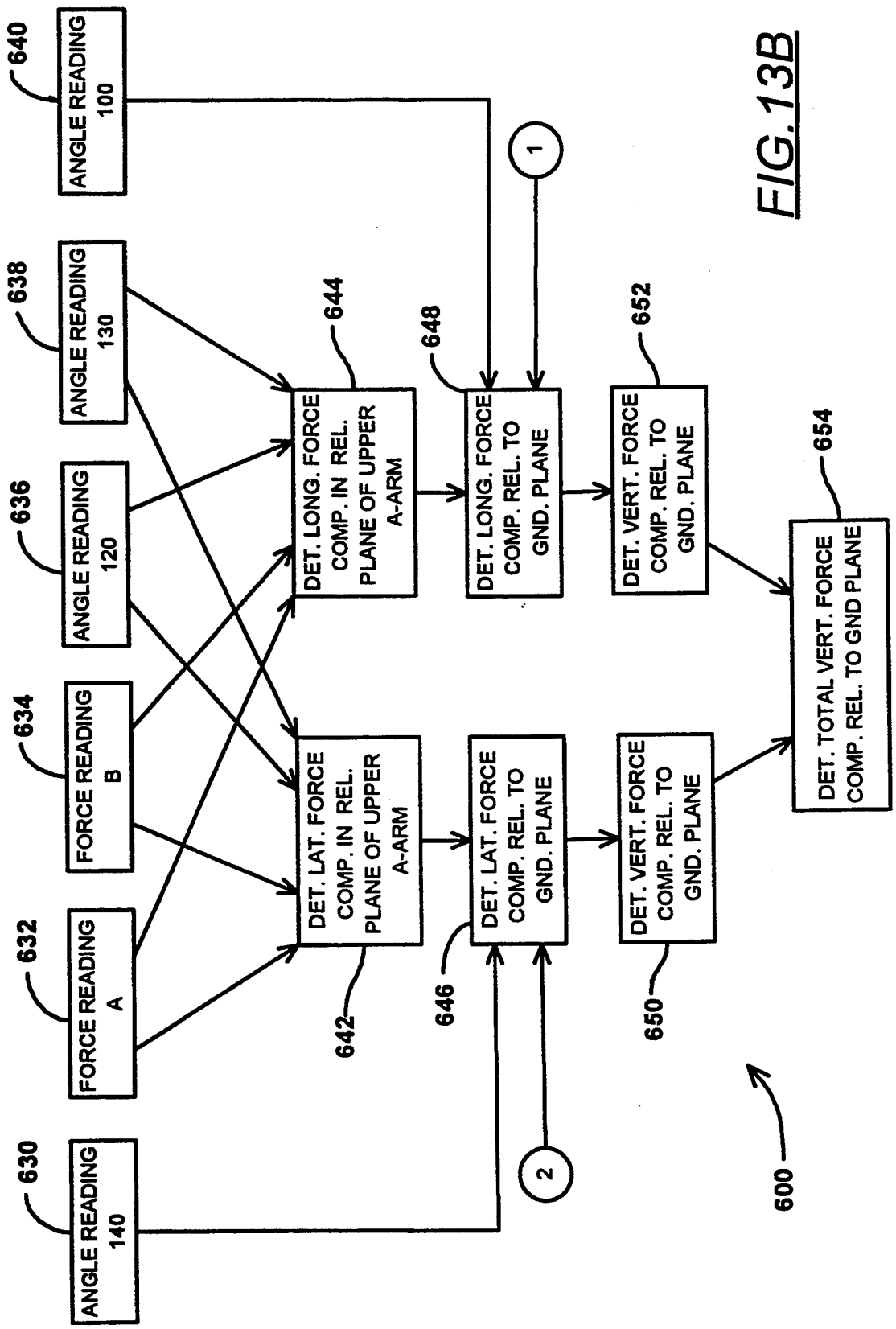

Looking next to FIG. 13B wherein the analysis of the load forces in upper A-arm 66b (FIG. 3) is considered, it is seen that sensor reading inputs additionally are received at blocks 630, 632, 634, 636, 638, and 640 as, respectively, angle reading 140, force reading A, force reading B, angle reading 120, angle reading 130, and angle reading 100. From blocks 632, 634, 636, and 638, load forces A and B, and angles 120 and 130 are received by block 642 wherein the lateral load force component in the relative plane of upper A-arm 66b is determined. In like manner, from blocks 632, 634, 636, and 638, load forces A and B, and angles 120 and 130 are received by block 644 wherein the longitudinal load force component in the relative plane of upper A-arm 66b is determined.

Next, blocks 646 and 648 are defined as receiving, respectively, the relative lateral load force component from block 642, and the relative longitudinal load force component from block 644, each for relation to ground plane 35 (FIG. 3). In this regard, block 646 receives angles γ and 140 from, respectively, blocks 622 (FIG.

13A) and 630, and block 648 receives angles θ and 100 from, respectively, blocks 620 (FIG. 13A) and 640. The normalized lateral and longitudinal load force components determined in blocks 646 and 648 are utilized, respectively, in blocks 650 and 652 for determining vertical components of the load force relative to ground plane 35, which vertical components are summed in block 654 to determine a total vertical load force relative thereto.

Figure 13C:
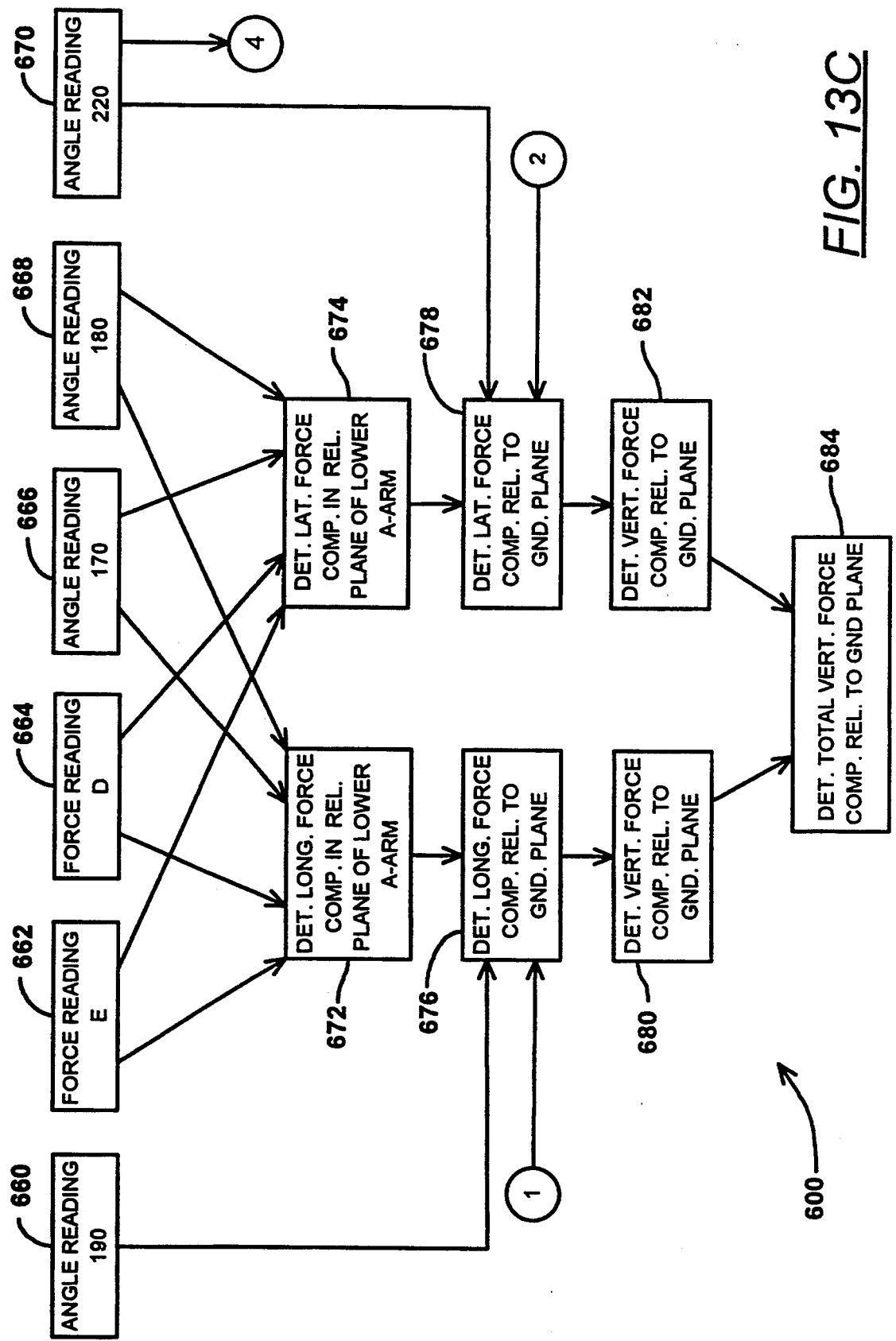

Continuing with FIG. 13C wherein the analysis continues with a consideration of the load forces on lower A-arm 68b (FIG. 3), additional sensor reading are received at blocks 660, 662, 664, 666, 668, and 670 as, respectively, angle reading 190, force reading E, force reading D, angle reading 170, angle reading 180, and angle reading 220. From blocks 662, 664, 666, and 668, load forces E and D, and angles 170 and 180 are received by block 672 wherein the longitudinal load force component in the relative plane of lower A-arm 68b is determined. In like manner, from blocks 662, 664, 666, and 668, load forces E and D, and angles 170 and 180 are received by block 674 wherein the lateral load force component in the relative plane of lower A-arm 68b is determined.

Blocks 676 and 682 next are defined as receiving, respectively, the relative longitudinal load force component from block 672, and the relative lateral load force component from block 674, each for relation to ground plane 35 (FIG. 3). In this regard, block 676 receives angles θ and 190 from, respectively, blocks 620 (FIG. 13A) and 660, and block 678 receives angles γ and 220 from, respectively, blocks 622 (FIG. 13A) and 670. The normalized longitudinal and lateral load force components determined in blocks 676 and 678 are utilized, respectively, in blocks 680 and 682 for determining vertical components of the load force relative to ground plane 35, which vertical components are summed in block 684 to determine a total vertical load force relative to ground plane 35.

Figure 13D:
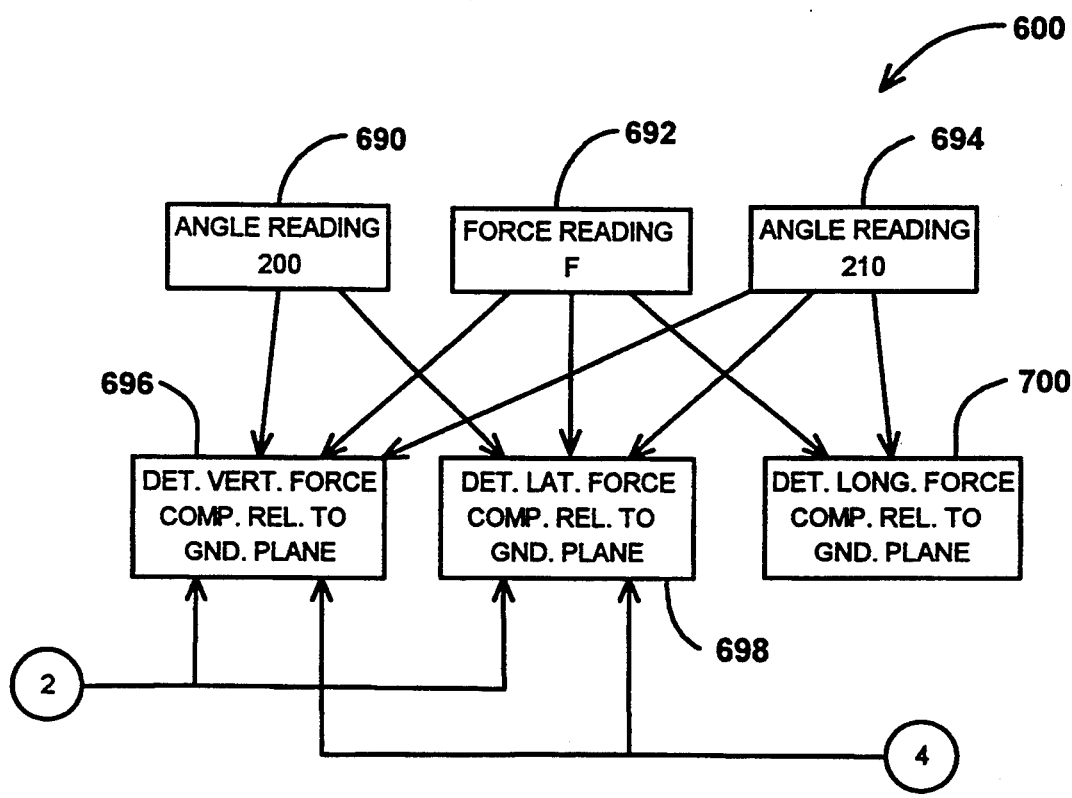

Proceeding to FIG. 13D, wherein diagram 600 continues with a consideration of the load forces in pushrod 76b (FIG. 3), sensor reading inputs are seen to be received at blocks 690, 692, and 694 as, respectively, angle reading 200, force reading F, and angle reading 210. From blocks 690, 692, and 694, angles 200 and 210, and load force F are received by block 696 for determining a vertical load force component relative to ground plane 35. Accordingly, block 696 additionally receives angle 220 from block 670 (FIG. 13C) and angle γ from block 622 (FIG. 13A). In like manner, angles 200 and 210, and load force F from blocks 690, 692, and 694, and angles 220 from block 670 and γ from block 622 are received by block 698 for determining a lateral load force component relative to ground plane 35. For determining longitudinal load force component relative to ground plane 35, block 700 is provided to receive force F from block 692 and angle 210 from block 694.

Figure 13E:
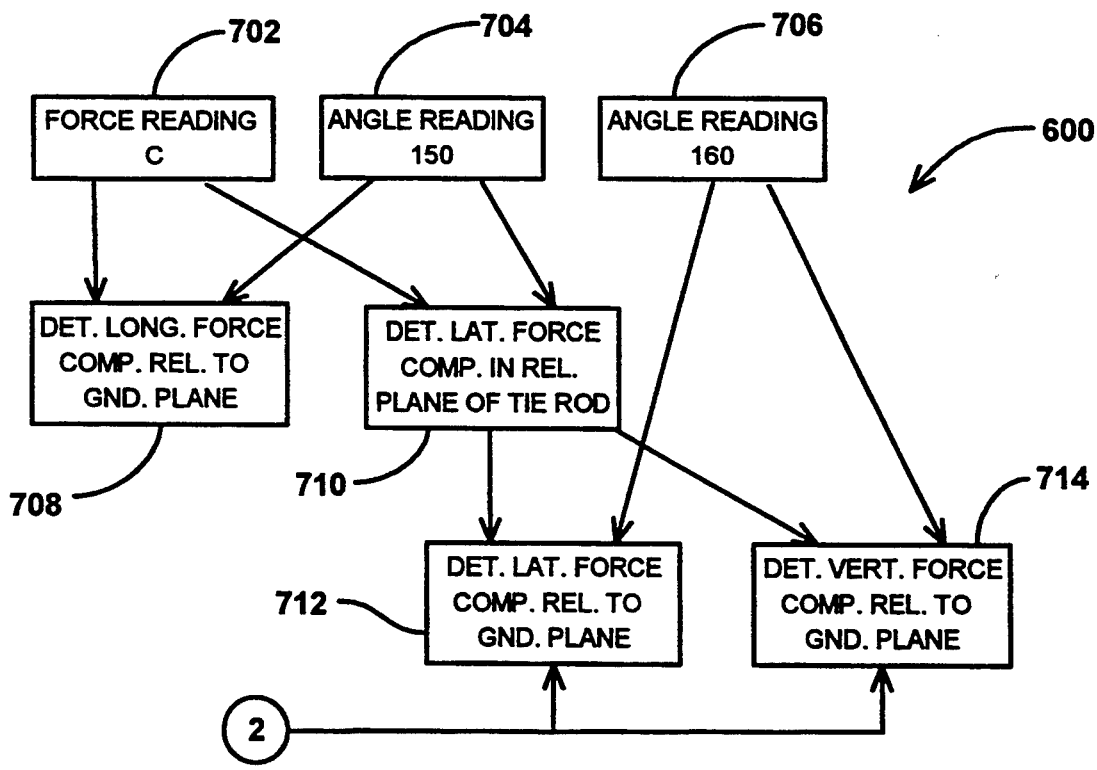

Looking next to FIG. 13E, wherein diagram 600 continues with an analysis of the load forces in tie rod 70b (FIG. 3), sensor reading inputs are shown to be received at blocks 702, 704, and 706 as, respectively, force reading C and angle readings 150 and 160. From blocks 702 and 704, force C and angle 150 are received by block 708 for determining a longitudinal load force component relative to ground plane 35, and by block 710 for determining a lateral force component in the relative plane of tie rod 70b. In turn, the relative lateral load force component determined in block 710 is utilized by block 712 for determining a lateral load force component normalized relative to ground plane, and by block 714 for determining a vertical load force component normalized relative to ground plane 35. In this regard, blocks 712 and 714 each additionally receive angle 160 from block 706 and angle γ from block 622 (FIG. 13A). Thus arranged, the operations defined by Eqs. 4–27 may be used to derive the total vertical, lateral, and longitudinal instantaneous grip forces within the contact patch at the interface of wheel 24b and ground plane 35.

Figure 13F:
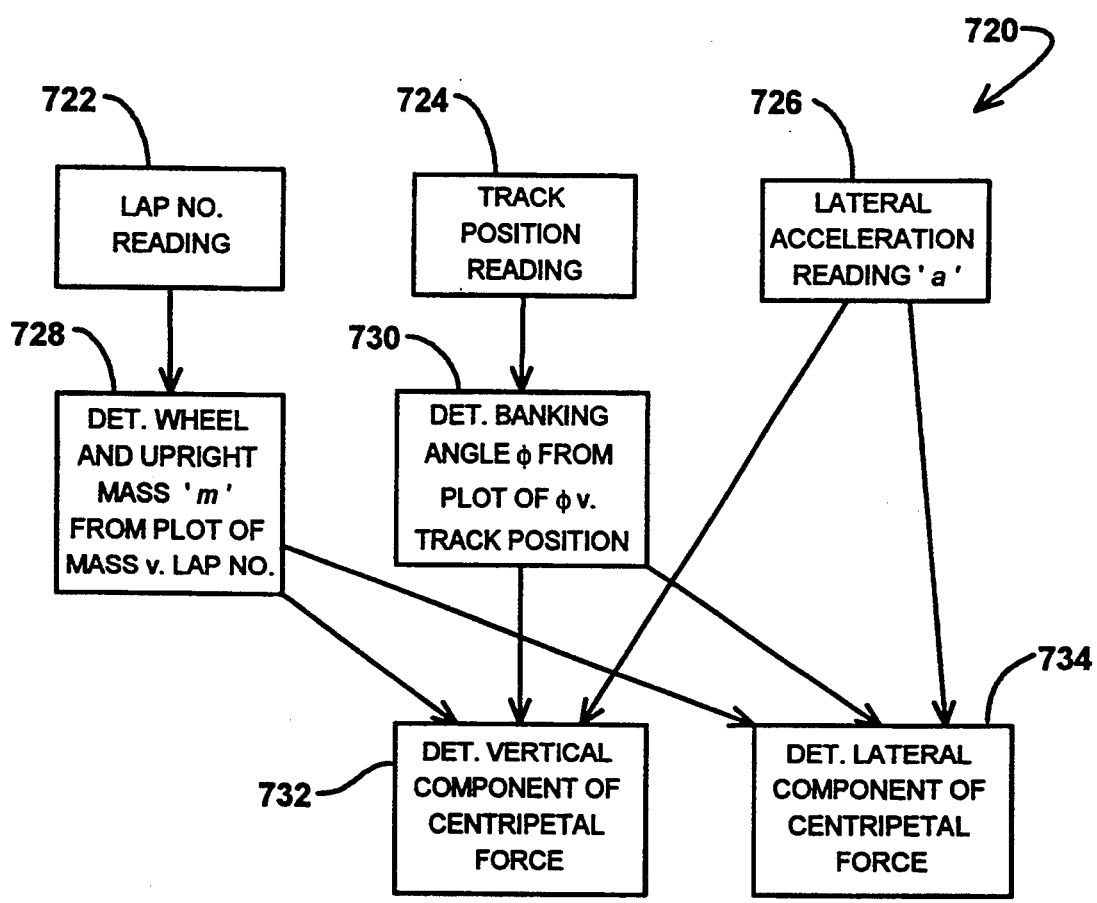
FIG. 13F is a block schematic diagram of a representative arrangement of operations for analyzing the centripetal forces acting on the wheel of FIG. 8.

Continuing with FIG. 13F, the analysis of wheel 24b proceeds with a consideration of the block diagram shown generally at 720 which presents an arrangement of operations for analyzing of the centripetal forces of Eqs. 28 and 29. In diagram 720, sensor readings are shown to be received at blocks 722, 724, and 726 as, respectively, a lap number reading, a track position reading, and lateral acceleration reading $a$. From the lap number reading of block 722, system mass m is determined at block 728 from an established plot of system mass versus lap number. In like manner, from the track position reading of block 724, banking angle φ is determined at block 730 from an established plot of φ versus track position. With the variables $a$, m, and φ being defined, a vertical component of centripetal force may be determined at block 732, with a lateral component of centripetal force being determined at block 734.

Figure 13G:
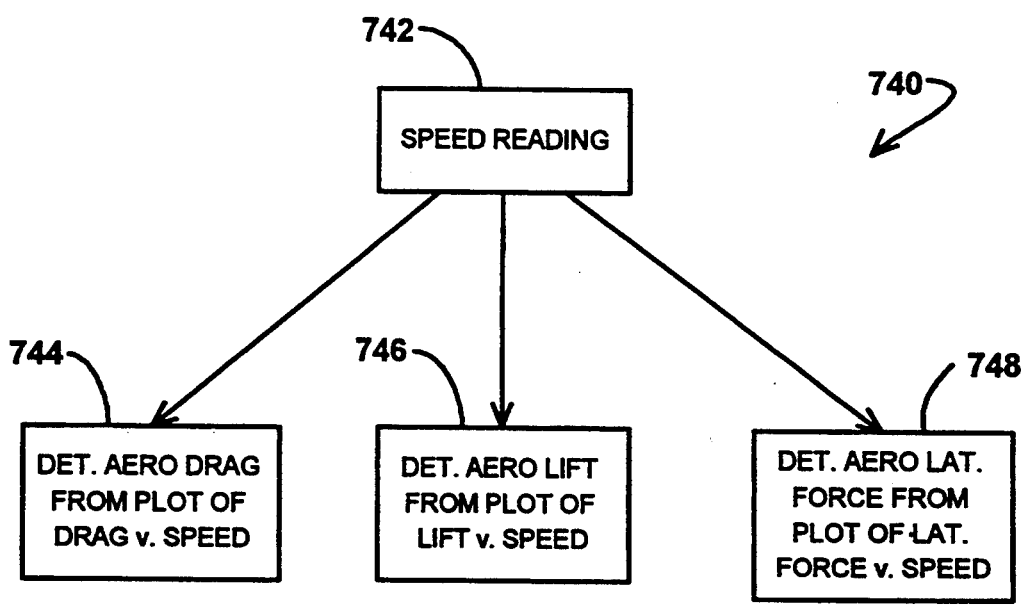
FIG. 13G is a block schematic diagram of a representative arrangement of operations for analyzing the aerodynamic forces graphically depicted in FIG. 10.

Proceeding to FIG. 13G and block diagram 740 thereof, the force balance about wheel 24b may be completed with an analysis of the aerodynamic forces acting thereon. In diagram 740, which presents an arrangement of operations for analyzing the aerodynamic drag, lift, and lateral forces shown graphically in FIG. 10, a sensor reading is shown to be received at block 742 as a car speed. From the speeding reading of block 742, the drag force component of the aerodynamic force is determined at block 744 from an established plot of drag versus speed. Similarly, the lift and lateral components of the aerodynamic force are determined at blocks 746 and 748 from corresponding plots of lift and of lateral force versus speed.

Turning now to FIGS. 14A–E wherein a diagram for the operations detailed in Eqs. 30–53 are shown in block schematic form generally at 800. Looking firstly to FIGS. 14A and 14E, it is seen that input parameters or sensor reading inputs are received at blocks 802, 804, 806, 808, 810, 812, 814, 816, 818, and 820 as, respectively, the values or readings designated, "w", "r", "f", "$L_o$", "o", "i", "$L_i$", "a", "b" and "c". In turn, block 820 receives inputs "w", "r", and "f" for determining attitude angle θ, block 822 receives inputs "$L_o$", "i", "o", and "$L_i$" for determining camber angle γ, and block 824 receives inputs "a", "b", and "c" for determining roll angle $a$. Additionally with respect to block 822, a steering rack displacement reading "M" is received at block 830 which, in turn, is received at block 832 wherein a relation is made to an established plot of "M" versus camber angle change Δγ. With camber angle γ and camber angle change Δγ being defined, camber angle γ is related to a transverse vertical plane through chassis 12 (FIG. 2) in block 834, which additionally receives an angle reading 500.

Figure 14A:
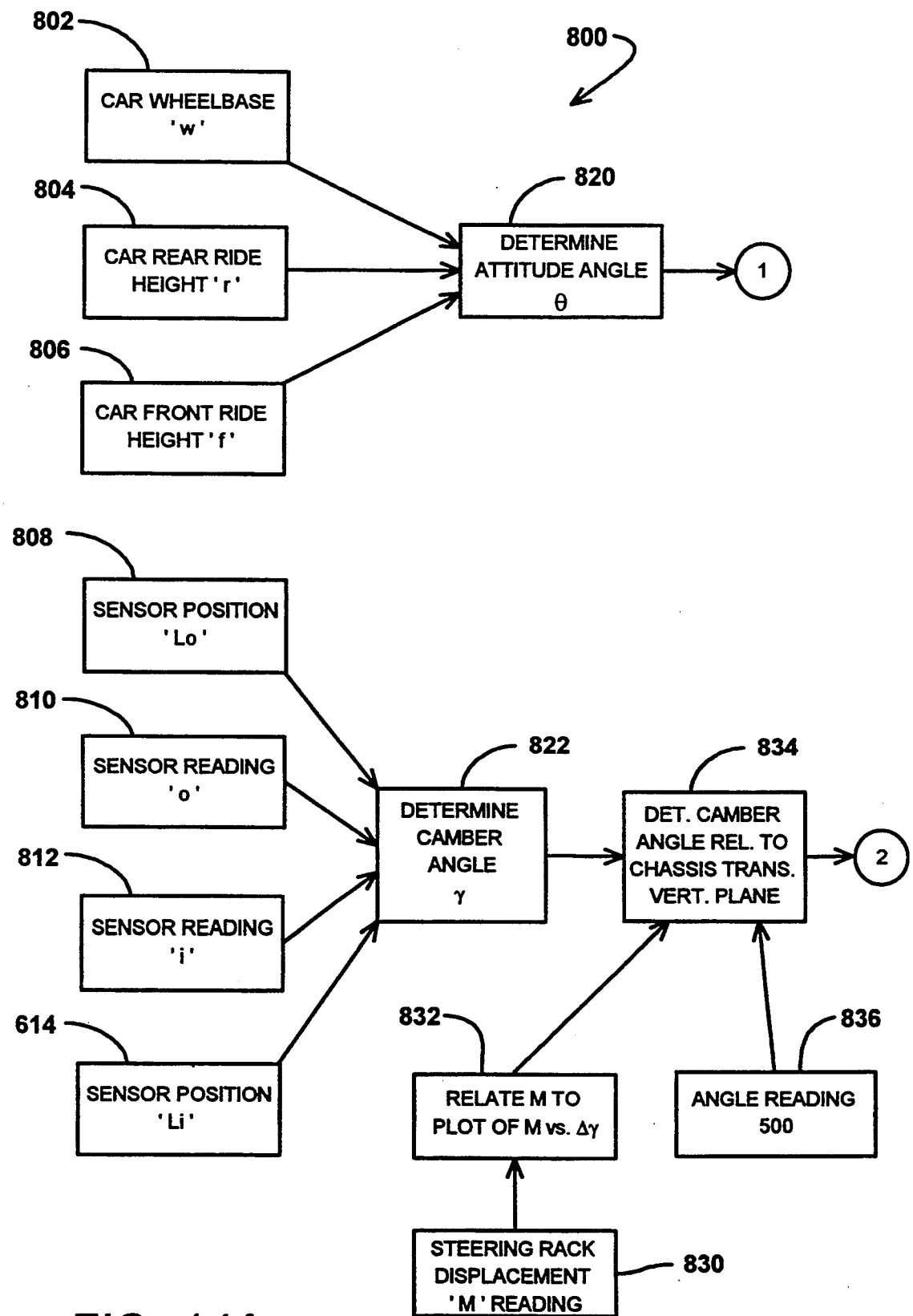
FIGS. 14A–E show a block schematic diagram of a representative arrangement of operations for analyzing the forces shown in the free body diagram of FIG. 12.
Figure 14B:
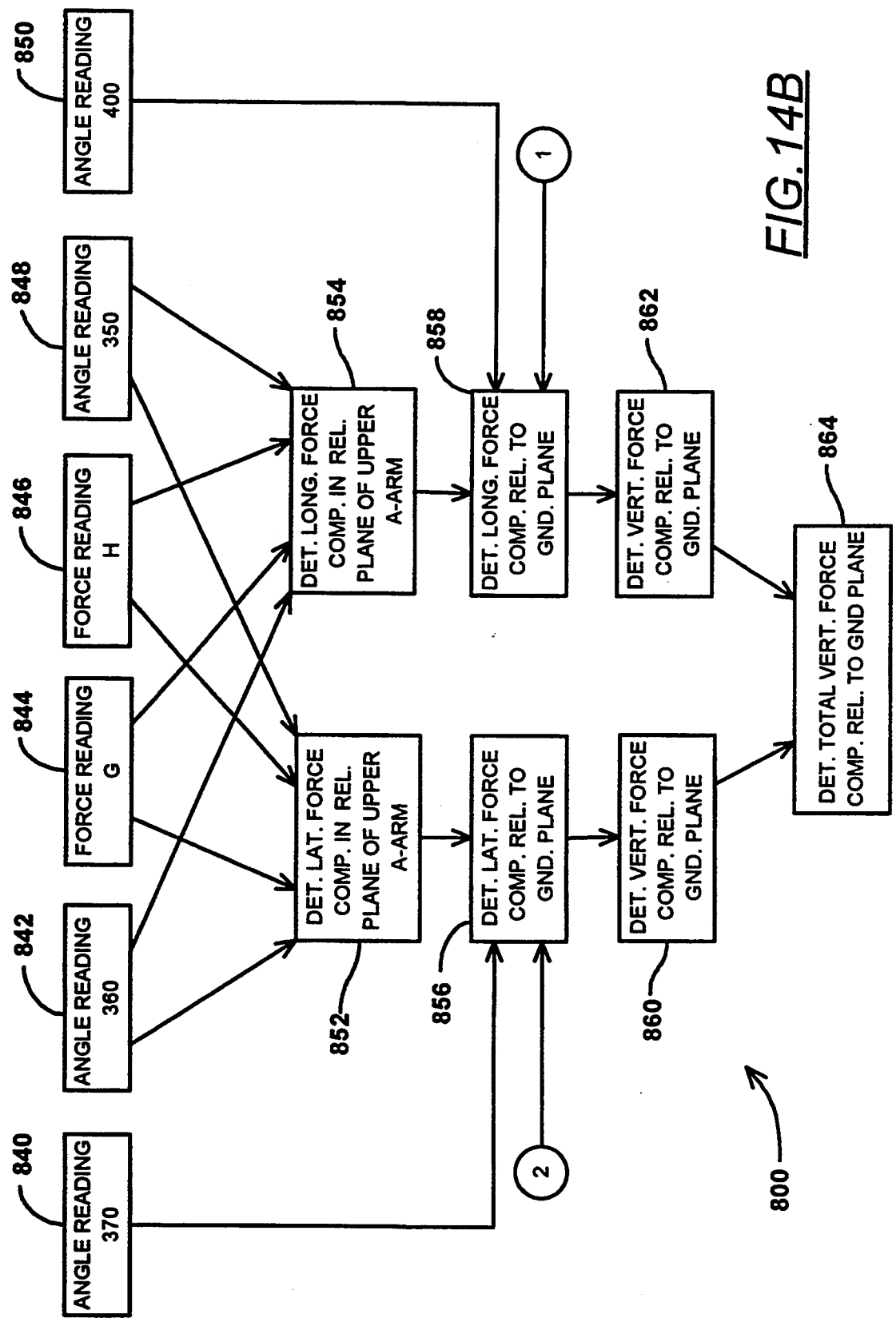

Looking next to FIG. 14B wherein the analysis of the load forces in upper A-arm 46b (FIG. 2) is considered, it is seen that sensor reading inputs additionally are received at blocks 840, 842, 844, 846, 848, and 850 as, respectively, angle readings 370 and 360, force readings G and H, and angle readings 350 and 400. From blocks 842, 844, 846, and 848, angles 360 and 350, and load forces G and H, and are received by block 852 wherein the lateral load force component in the relative plane of upper A-arm 46b is determined. In like manner, from blocks 842, 844, 846, and 848, angles 360 and 350, and load forces G and H are received by block 854 wherein the longitudinal load force component in the relative plane of upper A-arm 46b is determined.

Next, blocks 856 and 858 are defined as receiving, respectively, the relative lateral load force component from block 852, and the relative longitudinal load force component from block 854, each for relation to ground plane 35 (FIG. 2). In this regard, block 856 receives camber angle related to the transverse vertical plane through chassis 12 and angle 370 from, respectively, blocks 834 (FIG. 14A) and block 840. Further, block 858 receives angles $\theta$ and 400 from, respectively, blocks 820 (FIG. 14A) and 850. The normalized lateral and longitudinal load force components determined in blocks 856 and 858 are utilized, respectively, in blocks 860 and 862 for determining vertical components of the load force relative to ground plane 35, which vertical components are summed in block 864 to determine a total vertical load force relative thereto.

Figure 14C:
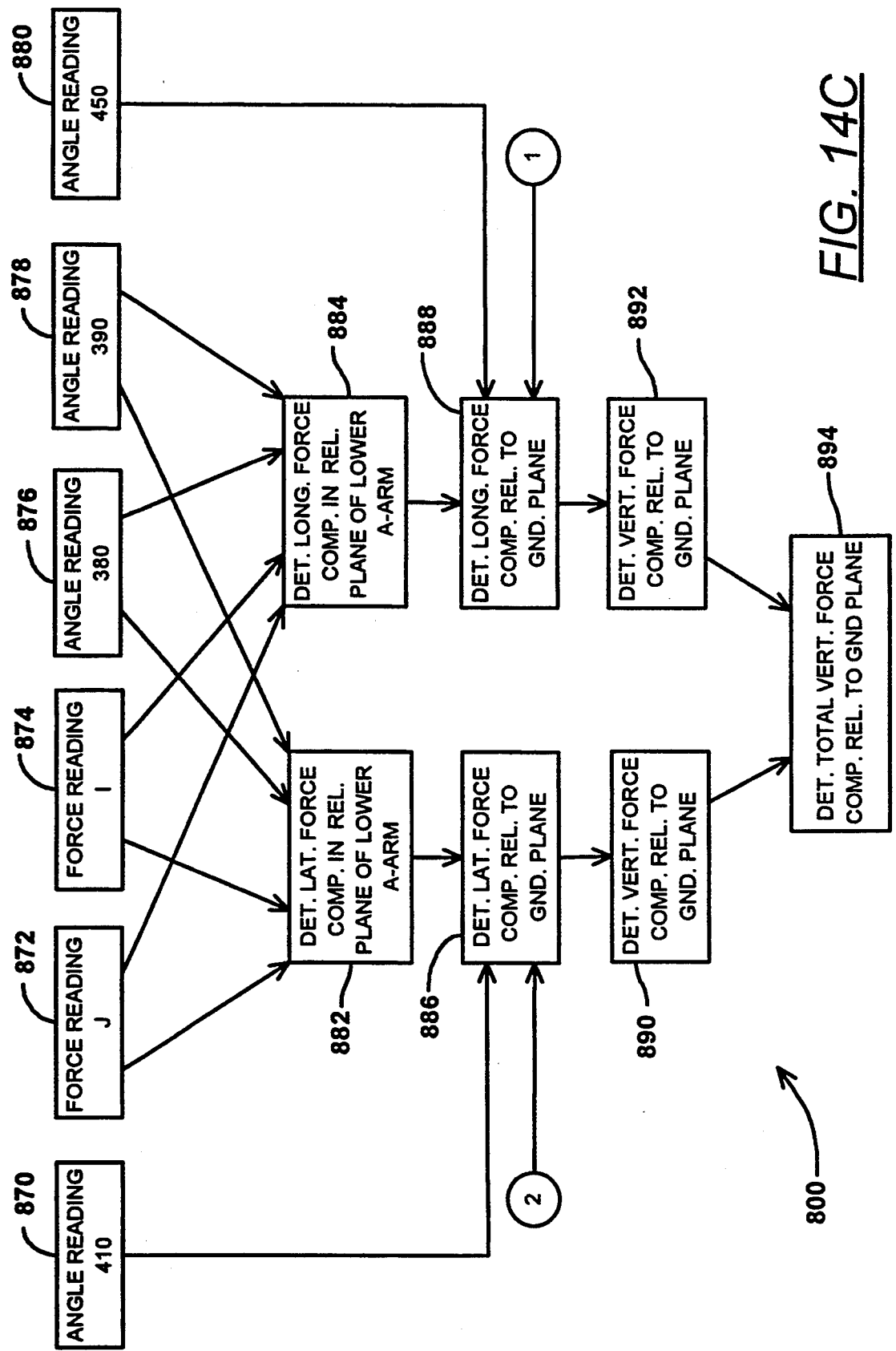

Continuing with FIG. 14C wherein the analysis continues with a consideration of the load forces on lower A-arm 48b (FIG. 2), additional sensor readings are received at blocks 870, 872, 874, 876, 878, and 880 as, respectively, angle reading 410, force reading J, force reading I, angle reading 380, angle reading 390, and angle reading 450. From blocks 872, 874, 876, and 878, load forces J and I, and angles 380 and 390 are received by block 882 wherein the lateral load force component in the relative plane of lower A-arm 48b is determined. In like manner, from blocks 872, 874, 876, and 878, load forces J and I, and angles 380 and 390 are received by block 884 wherein the longitudinal load force component in the relative plane of lower A-arm 68b is determined. Next, blocks 886 and 888 are defined as receiving, respectively, the relative lateral load force component from block 882, and the relative longitudinal load force component from block 884, each for relation to ground plane 35 (FIG. 2). In this regard, block 886 receives camber angle $\gamma$ related to the transverse vertical plane through chassis 12 and angle 410 from, respectively, blocks 834 (FIG. 14A) and block 870. Further, block 888 receives angles $\theta$ and 450 from, respectively, blocks 820 (FIG. 14A) and 880. The normalized lateral and longitudinal load force components determined in blocks 886 and 888 are utilized, respectively, in blocks 890 and 892 for determining vertical components of the load force relative to ground plane 35, which vertical components are summed in block 894 to determine a total vertical load force relative thereto.

Figure 14D:
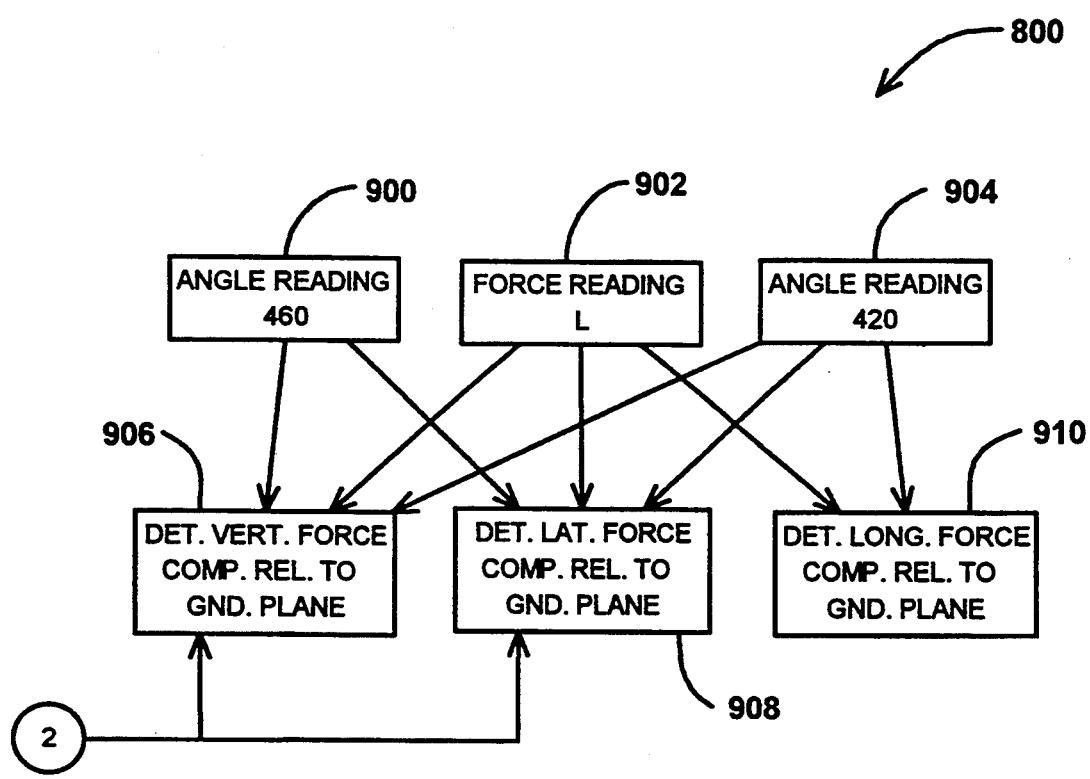

Proceeding to FIG. 14D, wherein diagram 800 continues with a consideration of the load forces in pushrod 54b (FIG. 2), sensor reading inputs are seen to be received at blocks 900, 902, and 904 as, respectively, angle reading 460, force reading L, and angle reading 420. From blocks 900, 902, and 904, angles 460 and 420, and load force L are received by block 906 for determining a vertical load force component relative to ground plane 35. Accordingly, block 906 additionally receives camber angle $\gamma$ related to the transverse vertical plane through chassis 12 from block 834 (FIG. 14A). In like manner, angles 460 and 420, and load force L from blocks 900, 902, and 904, and angle $\gamma$ related to the transverse vertical plane through chassis 12 from block 834 are received by block 908 for determining a lateral load force component relative to ground plane 35. For determining a longitudinal load force component relative to ground plane 35, block 910 is provided to receive force L from block 902 and angle 420 from block 904.

Figure 14E:
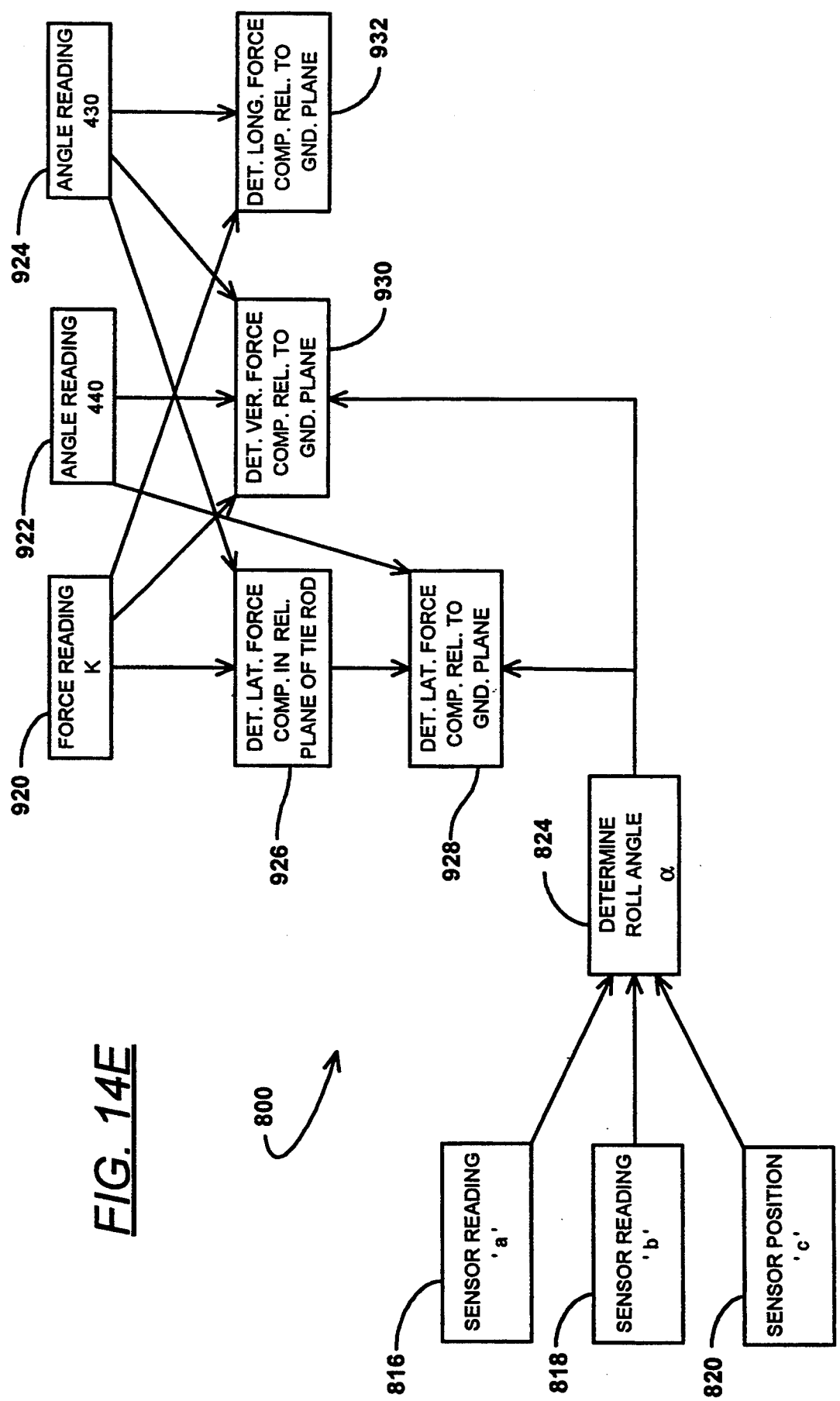

Looking next to FIG. 14E, wherein diagram 800 continues with an analysis of the load forces in steering tie rod 44b (FIG. 2), sensor reading inputs are shown to be received at blocks 920, 922, and 924 as, respectively, force reading K and angle readings 440 and 430. From blocks 920 and 924, force K and angle 430 are received by block 926 for determining a lateral load force component in the relative plane of steering tie rod 44b. In turn, the relative lateral load force component determined in block 926 is utilized by block 928, which additionally receives angle 440 from block 922 and roll angle $\alpha$ from block 824 (FIG. 14A), for determining a lateral load force component normalized relative to ground plane 35. 5For determining a vertical load force relative to ground plane 35, block 930 receives angles 440 and 430 from blocks 922 and 924, force reading K from block 920, and additionally roll angle $\alpha$ from block 824. Likewise, for determining a longitudinal load force component relative to ground plane 35, block 932 receives angle 430 from block 924 and force reading K from block 920. Thus arranged, the operations defined by Eqs. 30-53 may be used to derive the total vertical, lateral, and longitudinal instantaneous grip forces within the contact patch at the interface of wheel 20b and ground plane 35.

Looking next to FIG. 15, the application of the present system and method to the measurement of the grip forces at the wheels of a passenger car or the like is described in connection with the wheel and upright system shown generally at 1000. Wheel and upright system 1000 is seen to comprise a wheel, 1002, which is mounted on an axle, 1004, having an axle centerline, 1005, and which is positioned along a vertical centerline, 1006, to define a camber angle, $\gamma$, relative to the plane represented by line 1008 disposed vertically to the ground plane, 1010, upon which wheel 1002 rests. Axle 1004 is pivotally connected at coupling 10 12 to a first intermediate load member, 1014, which may be a toe link and which extends to a pivotal connection with a chassis, 1016, at coupling 1018. As did chassis 12 of road racing car 10, the lower surface of chassis 1016 defines a bottom plane, 1020, which, in turn, defines attitude angle $\theta$ (FIG. 4) with ground plane 1010.

For dampening shock forces to chassis 1016, a strutted piston member, which may be of the McPherson-type shown generally at 1021, is provided. Strut 1021 extends from chassis 1016 to an outboard upright portion, 1022, supporting axle 1004 along a longitudinal centerline, 1024, defining a predetermined angle, $\Gamma$, with the vertical centerline 1006 of wheel 1002. Strut 1021 is formed as having an outer spring, 1026, and an inner, strutted piston member, 1028, having a movable piston portion (not shown).

Additionally supporting chassis 1016 on wheel 1002 is a second intermediate load member, 1(30, which may be an A-arm, a wishbone, or the like. Second intermediate load member 1030 is provided as having a first end pivotally-coupled to chassis 1016 at universal joint 1032, and a second end pivotally-coupled to upright 1022 at universal joint 1034.

Figure 16:
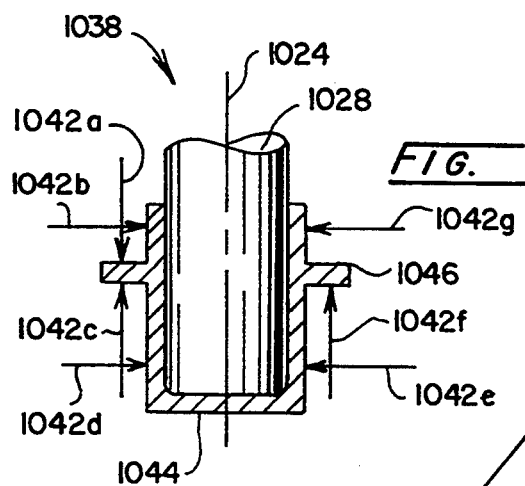
FIG. 16 shows the piston of the strut of FIG. 15 in enhanced detail revealing the placement of load cells about a load isolation member for isolating the piston from the upright.

As were the component members of suspensions 28 and 30 of road racing car 10, the suspension members of system 1000 similarly may be equipped with force sensors for measuring the instantaneous load force vectors acting thereon. Again, the force sensors may be located between the component members of system 1000 and chassis 10 16, directly on the component members, between the members and upright 1022, or, and as will be detailed hereinafter, between the bearings of axle 1004 and upright 1022. However, to facilitate instrumentation and data analysis, it is preferred to isolate members 1014, 1021, and 1030 From upright 1022 via, respectively the arrangements of load sensors represented at blocks 1036, 1037, 1038, 1040, and 1041. As is detailed in connection with FIG. 16 wherein load sensor arrangement 1038 is shown in enhanced detail, load sensors 1042a-g may be seen to be disposed either normal or parallel to longitudinal axis 1024 of strut 1021 for a simple summation of the forces measured. It will be appreciated that the load sensors comprising arrangements 1036 and 1040 similarly may be disposed either normal or parallel to axle centerline 1005 or wheel vertical centerline 1006 to facilitate force summation. With respect to load sensor arrangement 1038, a load isolation member, 1044, having a flanged portion, 1046, may be interposed between upright 1022 (FIG. 13) and strut 1021. In this way, and with load cells 1042 positioned between isolation member 1044 and upright 1022 as shown, strut 1021 and strutted piston member 1028 thereof are isolated from upright 1022. In like manner, sensor arrangements 1036, 1037, 1040, and 1041 may be configured as including load isolation members to facilitate force summation by isolating intermediate load members 1030 and 1014 from chassis 1016 and upright 1022.

Figure 17:
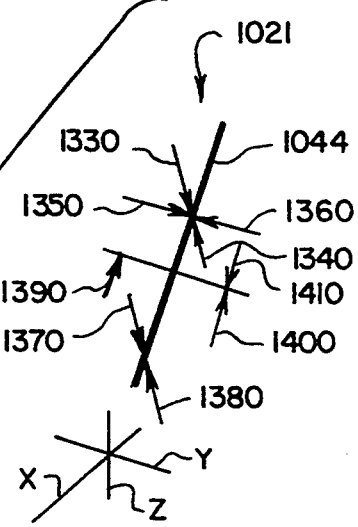
FIG. 17 is a free body diagram of the forces developed in the wheel and upright system of FIG. 15.
Figure 17:
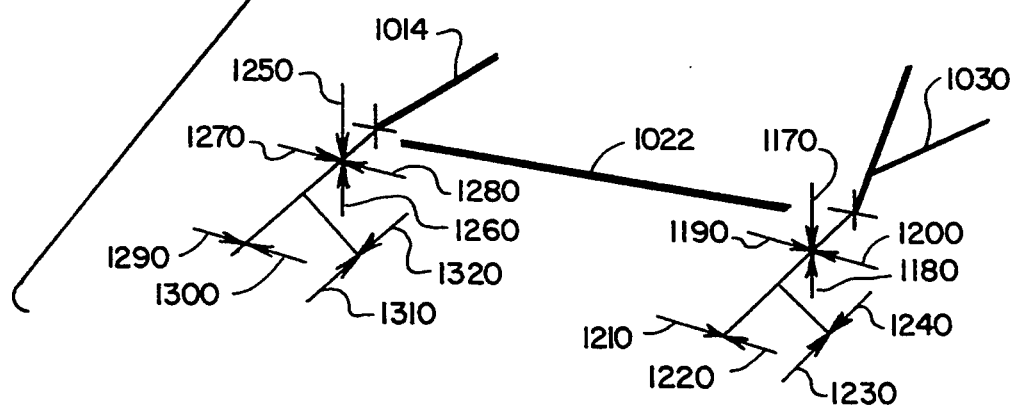

Turning to FIG. 17, the forces measured in the suspension elements comprising wheel and upright system 1000, namely, toe link 1014, strut 1021, and intermediate load member 1030 are presented for illustrative purposes in terms of a free body force diagram. To facilitate resolution of the forces measured and their relation to a common reference plane such as ground plane 1010, reference is made to the set of relative coordinate axes shown at $x$, $y$, and $z$ which are directed, respectively, in the lateral direction parallel to axle centerline 1005, in the longitudinal direction transverse to axle centerline 1005, and in the vertical direction parallel to wheel vertical centerline 1006 to thereby define the relative horizontal, lateral, and vertical planes of upright 1022. Further, definition of the following values with reference to the relative coordinate axes x, y, and z is helpful:

TABLE 4

Force 1170 on intermediate load member 1030 in the relative vertical plane of upright 1022;
Force 1180 on intermediate load member 1030 in the relative vertical plane of upright 1022;
Force 1190 on intermediate load member 1030 in the relative longitudinal plane of upright 1022;
Force 1200 on intermediate load member 1030 in the relative longitudinal plane of upright 1022;
Force 1210 on intermediate load member 1030 in the relative longitudinal plane of upright 1022;
Force 1220 on intermediate load member 1030 in the relative longitudinal plane of upright 1022;
Force 1230 on intermediate load member 1030 in the relative lateral plane of upright 1022;
Force 1240 on intermediate load member 1030 in the relative lateral plane of upright 1022;
Force 1250 on toe link 1014 in the relative vertical plane of upright 1022;
Force 1260 on toe link 1014 in the relative vertical plane of upright 1022;

TABLE 4-continued

Force 1270 on toe link 1014 in the relative longitudinal plane of upright 1022;
Force 1280 on toe link 1014 in the relative longitudinal plane of upright 1022;
Force 1290 on toe link 1014 in the relative longitudinal plane of upright 1022;
Force 1300 on toe link 1014 in the relative longitudinal plane of upright 1022;
Force 1310 on toe link 1014 in the relative lateral plane of upright 1022;
Force 1320 on toe link 1014 in the relative lateral plane of upright 1022;
Force 1330 on strut 1021 load isolation member 1044;
Force 1340 on strut 1021 load isolation member 1044;
Force 1350 on strut 1021 load isolation member 1044 in the relative longitudinal plane of upright 1022;
Force 1360 on strut 1021 load isolation member 1044 in the relative longitudinal plane of upright 1022;
Force 1370 on strut 1021 load isolation member 1044;
Force 1380 on strut 1021 load isolation member 1044;
Force 1390 on strut 1021 load isolation member 1044;
Force 1400 on strut 1021 load isolation member 1044;
Force 1410 on strut 1021 load isolation member 1044;
Attitude angle $\theta$ between ground plane 1010 and bottom plane 1020 of chassis 1016;
Camber angle $\gamma$ relative to ground plane 1020; and
Strut angle $\beta$ relative to wheel vertical centerline 1006.

Again, angles $\theta$ and $\gamma$ may be determined as explained in connection with FIGS. 4 and 5, with angle $\beta$ being defined as explained in connection with FIG. 13. With angles $\theta$, $\gamma$, and $\beta$ thus being defined, the analysis may proceed to a consideration as follows of the forces acting on load isolation member 1044 of strut 1021, wherein all numbers relate to reference numerals rather than to numerical quantifies except where noted:

(a) Vertical load force in the relative plane of upright 1022:
$$(1340 - 1330)\sin\beta + (1380 - 1370)\sin\beta + (1390 - 1400 - 1410)\cos\beta \quad (54)$$
(b) Lateral load force in the relative plane of upright 1022:
$$(1340 - 1330)\cos\beta + (1380 - 1370)\cos\beta + (1410 - 1390 - 1400)\sin\beta \quad (55)$$
(c) Longitudinal load force in the relative plane of upright 1022:
$$1350 - 1360 \quad (56)$$
Considering next the forces action on toe link 1014 as follows:
(a) Vertical load force in the relative plane of upright 1022:
$$1260 - 1250 \quad (57)$$
(b) Lateral load force in the relative plane of upright 1022:
$$1320 - 1310 \quad (58)$$
(c) Longitudinal load force in the relative plane of upright 1022:
$$1270 + 1290 - 1300 - 1280 \quad (59)$$
Considering also the forces acting on intermediate load member 1030 as follows:
(a) Vertical load force in the relative plane of upright 1022:
$$1180 - 1170 \quad (60)$$
(b) Lateral load force in the relative plane of upright 1022:
$$1240 - 1230 \quad (61)$$
(c) Longitudinal load force in the relative plane of upright 1022:
$$1190 + 1210 - 1220 - 1200 \quad (62)$$
Summing the forces derived in Eqs. 54–62 to derive total lateral, longitudinal, and vertical forces in the relative plane of upright 1022:
(a) Total vertical load force in the relative plane of upright 1022:
$$(1340 - 1330)\sin\beta + (1380 - 1370)\sin\beta + (1390 - 1400 - 1410)\cos\beta + 1260 - 1250 + 1180 - 1170 \quad (63)$$
(b) Total lateral load force in the relative plane of upright 1022:
$$(1340 - 1330)\cos\beta + (1380 - 1370)\cos\beta + (1410 - 1390 - 1400)\sin\beta + 1320 - 1310 + 1240 - 1230 \quad (64)$$
(c) Total longitudinal load force in the relative plane of upright 1022:

-continued $$1350 - 1360 + 1270 + 1290 - 1300 - 1280 + 1190 + 1210 - 1220 - 1200 \quad (65)$$

Normalizing the totaled vertical forces of Eq. 63 to ground plane 1010:
(a) Normalized vertical load force component:
$$- \text{Eq. } 63/\sqrt{((1 + (\tan \gamma)^2 + (\tan \theta)^2)} \quad (66)$$
(b) Normalized lateral load force component:
$$(- \text{Eq. } 63) \tan \theta/\sqrt{((1 + (\tan \gamma)^2 + (\tan \theta)^2)} \quad (67)$$
(c) Normalized longitudinal load force component:
$$(- \text{Eq. } 63) \tan \gamma/\sqrt{((1 + (\tan \gamma)^2 + (\tan \theta)^2)} \quad (68)$$

Normalizing the totaled longitudinal forces of Eq. 65 to ground plane 1010:
(a) Normalized vertical load force component:
$$\text{Eq. } 65/\sqrt{((1/\cos \gamma)^2 + (1/\sin \theta)^2 - 1)} \quad (69)$$
(b) Normalized lateral load force component:
$$((- \text{Eq. } 65) \tan \theta)/\sqrt{((1/\cos \gamma)^2 + (1/\sin \theta)^2 - 1)} \quad (70)$$
(c) Normalized longitudinal load force component:
$$((- \text{Eq. } 65)/(\tan \gamma \sqrt{((1/\cos \gamma)^2 + (1/\sin \theta)^2 - 1)}) \quad (71)$$

Normalizing the totaled lateral forces of Eq. 64 to ground plane 1010:
(a) Normalized vertical load force component:
$$\text{Eq. } 64/\sqrt{((1/\sin \gamma)^2 + (1/\cos \theta)^2 - 1)} \quad (72)$$
(b) Normalized lateral load force component:
$$((\text{Eq. } 64)/(\tan \gamma \sqrt{((1/\sin \gamma)^2 + (1/\cos \theta)^2 - 1)})) \quad (73)$$
(c) Normalized longitudinal load force component:
$$((\text{Eq. } 64) \tan \theta)/\sqrt{((1/\sin \gamma)^2 + (1/\cos \theta)^2 - 1)} \quad (74)$$

From Eqs. 66–74, an instantaneous total force balance on system 1000 may be determined with respect to ground plane 1010 for use as an objective criteria upon which may be assessed the comparative grip performance of wheel 1002. Moreover, and as detailed hereinbefore in connection with road racing car 10, a total force balance also may be derived which includes the influences of the centripetal and aerodynamic forces acting on wheel 1002.

Considering FIGS. 18A–D, the operations detailed in Eqs. 54–74 are shown in block diagrammatic form generally at 1500. Looking firstly to FIG. 18A, it is seen that input parameters or sensor reading inputs are received at blocks 1510, 1520, 1530, 1540, 1550, 1560, 1570, and 1580 as, respectively, the values or readings designated, "w", "r", "f", "$L_o$", "o", "i", "$L_i$", and "B". In turn, block 1600 receives inputs "w", "r", and "f" for determining attitude angle $\theta$, and block 1610 receives inputs "$L_o$", "i", "o", and "$L_i$" for determining camber angle $\gamma$.

Figure 18A:
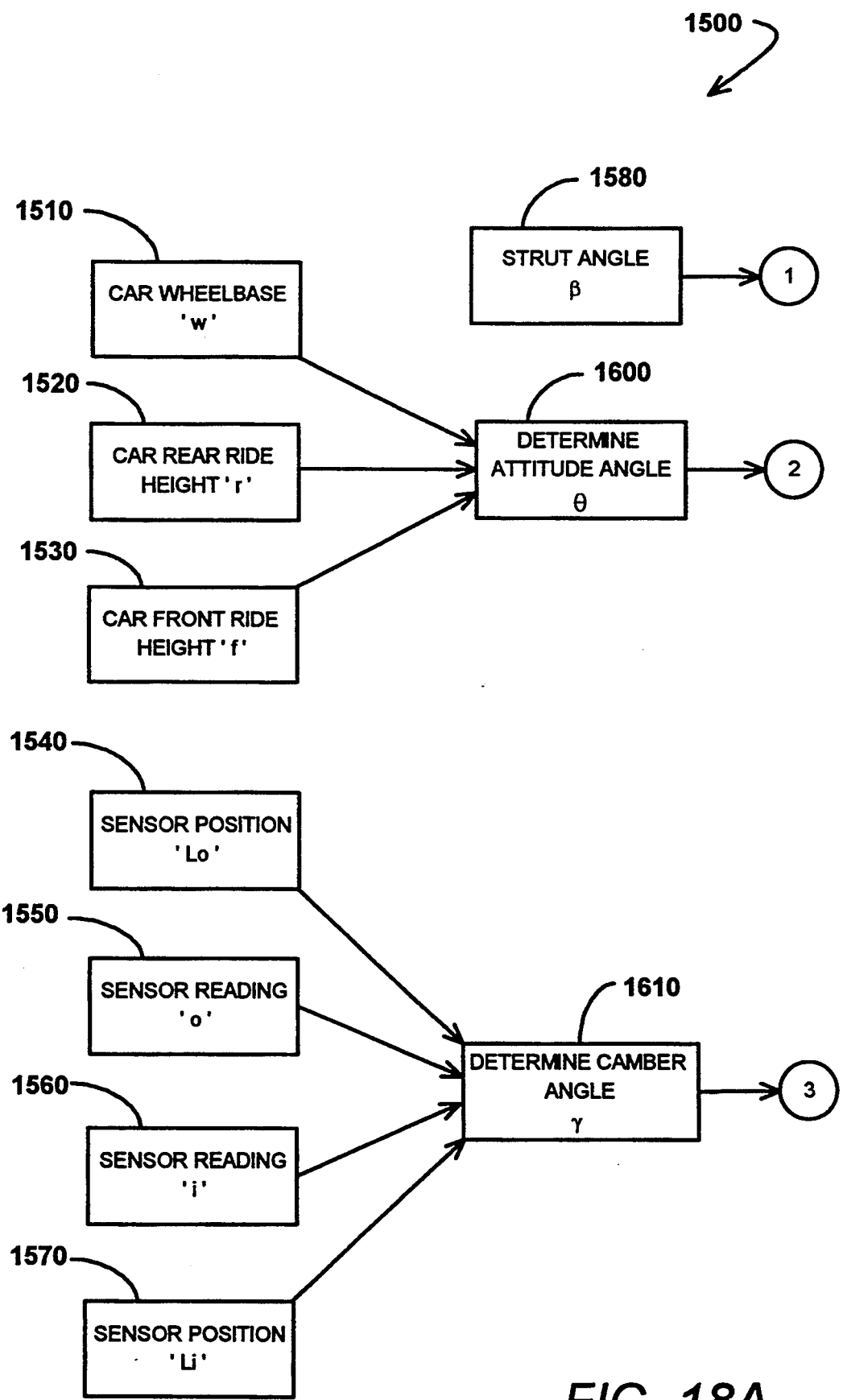
FIGS. 18A–D show a block schematic diagram of a representative arrangement of operations for analyzing the forces shown in the free body diagram of FIG. 17.
Figure 18B:
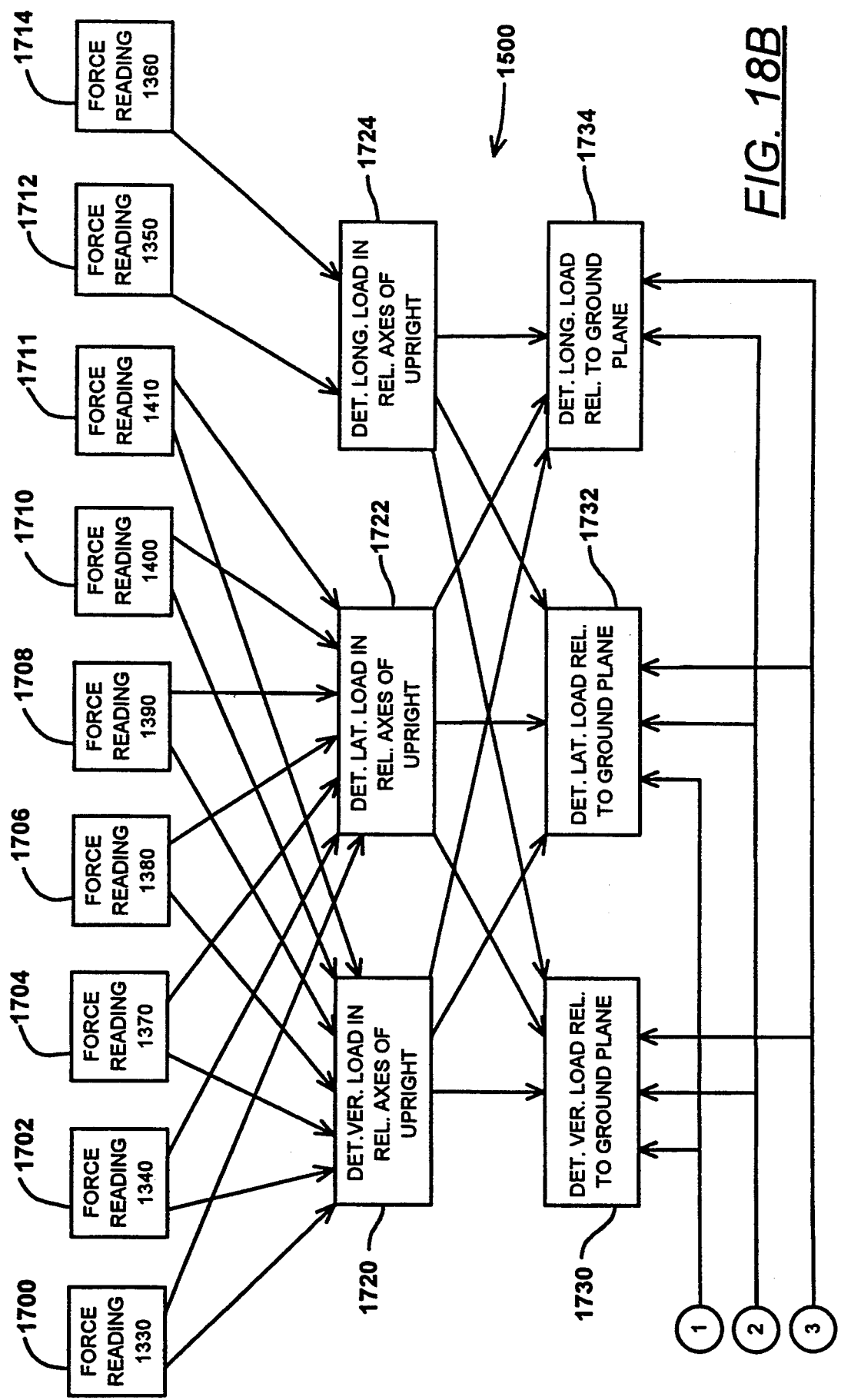

Looking next to FIG. 18B wherein the analysis of the load forces in strut 1021 (FIG. 15) is considered, it is seen that sensor reading inputs are also received blocks 1700, 1702, 1704, 1706, 1708, 1710, 1711, 1712, and 1714 as, respectively, load forces 1330, 1340, 1370, 1380, 1390, 1400, 1410, 1350, and 1360. From blocks 1700, 1702, 1704, 1706, 1708, 1710, and 1711, load forces 1330, 1340, 1370, 1380, 1390, 1400, and 1410 are received by block 1720 wherein the vertical load in the relative axes of upright 1022 (FIG. 15) is determined. In like manner, from blocks 1700, 1702, 1704, 1706, 1708, 1710, and 1711, load forces 1330, 1340, 1370, 1380, 1390, 1400, and 1410 are received by block 1722 wherein the lateral load in the relative axes of the upright is determined. Similarly, block 1724 receives load forces 1350 and 1360 from, respectively, blocks 1712 and 1714 for determining the longitudinal load forces relative to the axes of the upright.

Figure 15:
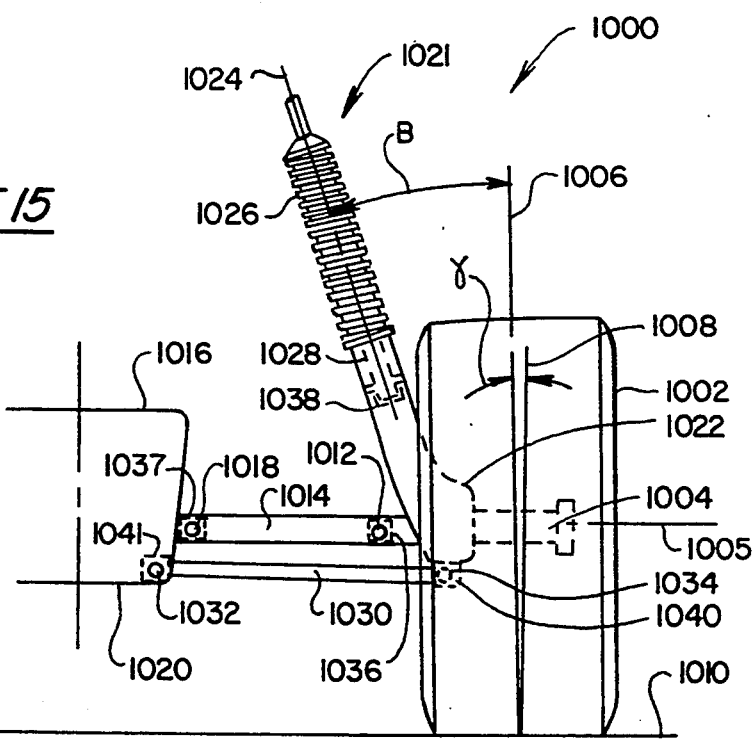
FIG. 15 is a schematic illustration, partially in cross-section, of a representative wheel and upright system of a passenger car which system includes a McPherson strut.

Next, blocks 1730, 1732, and 1734 are defined as receiving, respectively, the relative vertical load forces from block 1720, the relative lateral load forces from block 1722, and the relative longitudinal load forces from block 1724, each for relation to ground plane 1010 (FIG. 15). In this regard, blocks 1730 and 1732 each receive angles $\beta$, $\theta$, and $\gamma$ from, respectively, blocks 1580, 1600, and 1610 of FIG. 18A for determining the vertical, lateral, and longitudinal components of the load force on strut 1021 relative to the ground plane. Further in this regard, block 1734 receives angle $\theta$ from block 1600 and angle $\gamma$ from block 1610 of FIG. 18A.

Figure 18C:
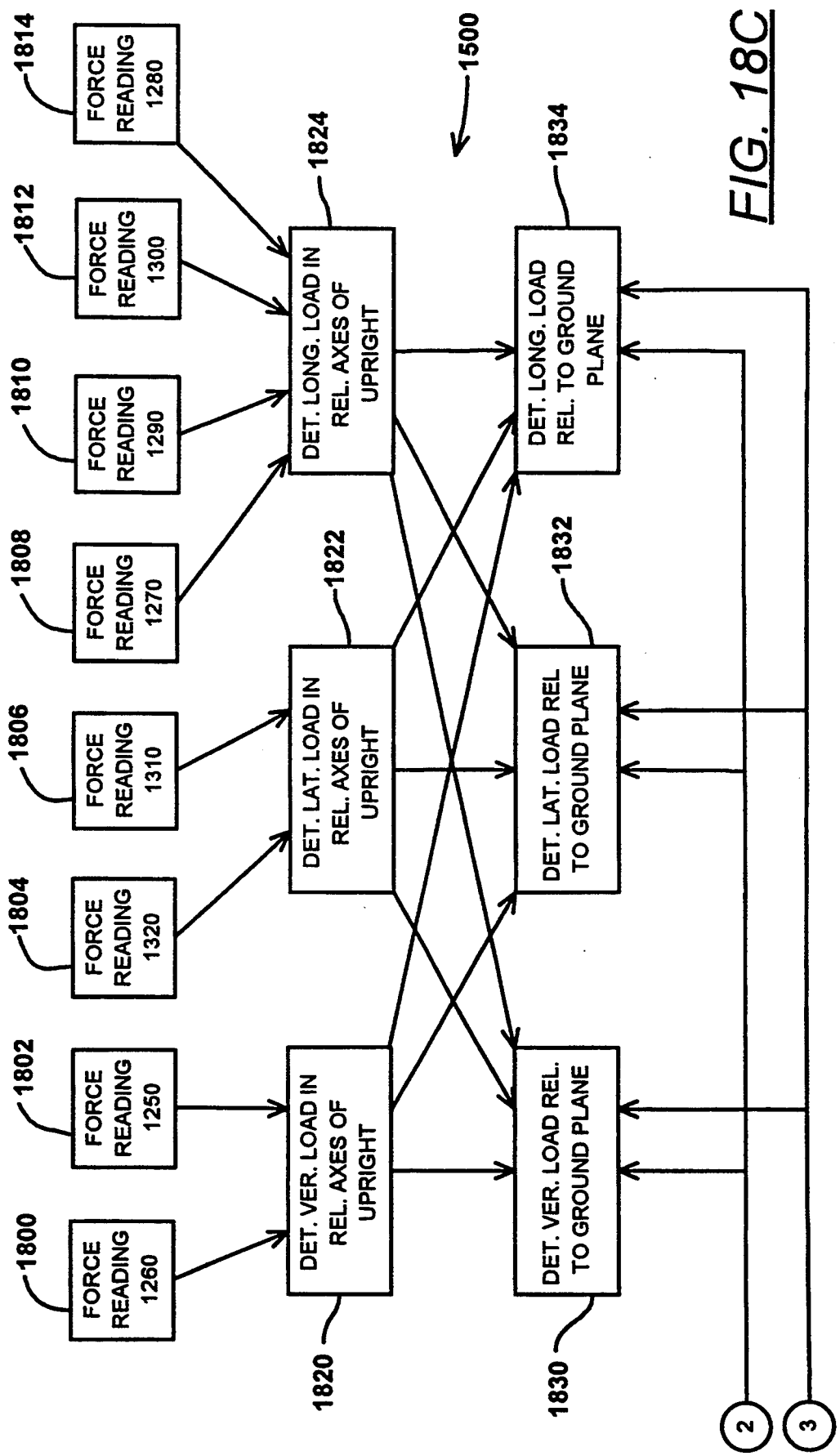

Continuing with FIG. 18C wherein the analysis continues with a consideration of the load forces on toe link 1014 (FIG. 15), sensor reading inputs are shown to be received by blocks 1800, 1802, 1804, 1806, 1808, 1810, 1812, and 1814 as, respectively, load forces 1260, 1250, 1320, 1310, 1270, 1290, 1300, and 1280. From blocks 1800 and 1802, load forces 1260 and 1250 are received by block 1820 wherein the vertical load in the relative axes of upright 1022 (FIG. 15) is determined. In like manner, from blocks 1804 and 1806, load forces 1320 and 1310 are received by block 1822 wherein the lateral load in the relative axes of the upright is determined. Similarly, block 1824 receives load forces 1270, 1290, 1300, and 1280 from, respectively, blocks 1808, 1810, 1812, and 1814 for determining the longitudinal load forces relative to the axes of the upright.

Blocks 1830, 1832, and 1834 next are defined as receiving, respectively, the relative vertical load forces from block 1820, the relative lateral load forces from block 1822, and the relative longitudinal load forces from block 1824, each for relation to ground plane 1010 (FIG. 15). In this regard, blocks 1830, 1832, and 1834 each receive angles $\theta$ and $\gamma$, from, respectively, blocks 1600 and 1610 of FIG. 18A for determining the vertical, lateral, and longitudinal components of the load force on toe link 1014 relative to the ground plane.

Figure 18D:
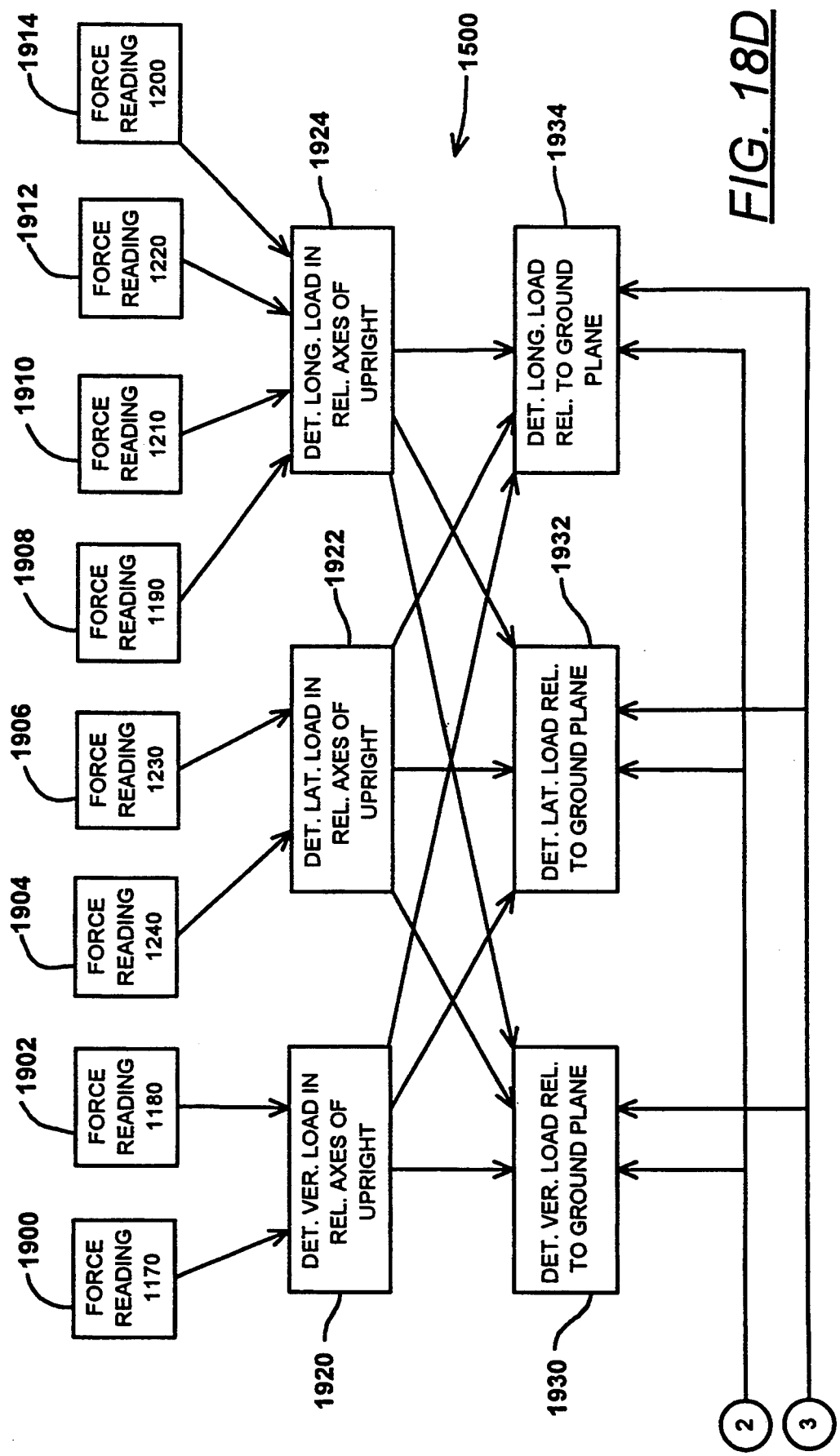

Continuing with FIG. 18D wherein the analysis continues with a consideration of the load forces on intermediate load member 1030 (FIG. 15), sensor reading inputs are shown to be received by blocks 1900, 1902, 1904, 1906, 1908, 1910, 1912, and 1914 as, respectively, load forces 1170, 1180, 1240, 1230, 1190, 1210, 1220, and 1200. From blocks 1900 and 1902, load forces 1170 and 1180 are received by block 1920 wherein the vertical load in the relative axes of upright 1022 (FIG. 15) is determined. In like manner, from blocks 1904 and 1906, load forces 1240 and 1230 are received by block 1922 wherein the lateral load in the relative axes of the upright is determined. Similarly, block 1924 receives load forces 1190, 1210, 1220, and 1200 from, respectively, blocks 1908, 1910, 1912, and 1914 for determining the longitudinal load forces relative to the axes of the upright.

Blocks 1930, 1932, and 1934 next are defined as receiving, respectively, the relative vertical load forces from block 1920, the relative lateral load forces from block 1922, and the relative longitudinal load forces from block 1924, each for relation to ground plane 1010 (FIG. 15). In this regard, blocks 1930, 1932, and 1934 each receive angles $\theta$ and $\gamma$, from, respectively, blocks 1600 and 1610 of FIG. 18A for determining the vertical, lateral, and longitudinal components of the load force on intermediate load member 1030 relative to the ground plane. Thus arranged., the operations defined by Eqs. 75–89 may be used to derive the total vertical, lateral, and longitudinal instantaneous grip forces within the contact patch at the interface of wheel 1002 and the ground plane.

Figure 19:
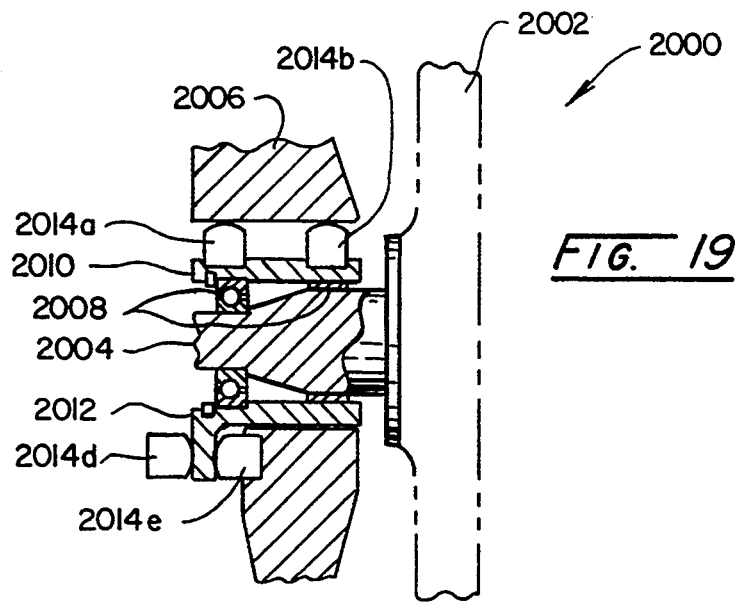
FIG. 19 is a schematic illustration in cross-section of a representative wheel and upright system including, in accordance with the present invention, an intermediate load member between the axle and the upright thereof.

Looking next to FIG. 19, an alternative arrangement for effecting the precepts of the present invention, which arrangement is suitable for implementation in any type of suspension, is shown in connection with a schematic illustration of the representative wheel and upright system shown generally at 2000. Wheel and upright system 2000 may be seen to comprise a wheel, 2002, supported on an axle, 2004, which, in turn, is supported by an upright, 2006. For allowing the rotation of axle 2004 within upright 2006, bearings, 2008, are interposed therebetween. In general, the alternative arrangement to be described is provided to measure the load forces acting as between the axle and the upright, rather than the load forces acting on the suspension members or as between the suspension members and the upright or chassis. Thus, in accordance with the present invention herein involved, a load carrier member, 2010, which may be configured as having a ranged portion, 2012, is interposed between axle 2004 and upright 2006. As is shown at 2014a, 2014b, 2014d, and 2014e, force sensors, which preferably are of the load cell-type, are disposed between load carrier member 20 10 and upright 2006 in order to isolate axle 2004 and wheel 2002 from upright 2006. A third load cell pair (not shown) additionally may be employed to complete the instrumentation of system 2000.

Figure 20:
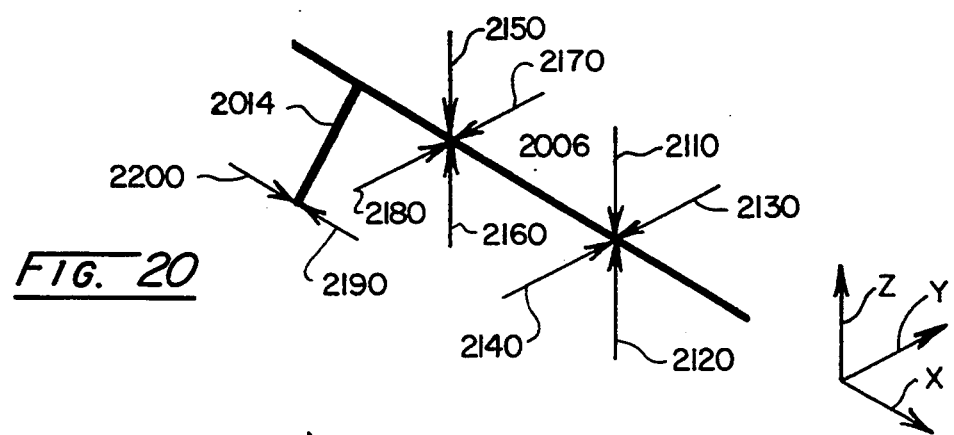
FIG. 20 is a free body diagram of the force vectors developed in the intermediate load member of FIG. 15.

Turning to FIG. 20, the forces measured with respect to intermediate load carrier member 20 10 are presented in terms of a free body diagram in relation to the set of relative coordinate axes shown at x, y, and z which are directed, respectively, to the relative lateral, longitudinal, and vertical axes of upright 2006. With the load forces measured on intermediate load carrier 2010 and flange portion 2014 thereof being shown at 2110, 2120, 2130, 2140, 2150, 2160, 2170, 2180, 2190, and 2200, the following load force components may be derived with relation to the relative lateral, longitudinal, and vertical axes of upright 2006:

(a) Vertical load force in the relative plane of upright 2006:
$$2120 + 2160 - 2150 - 2110 \quad (75)$$
(b) Lateral load force in the relative plane of upright 2006:
$$2200 - 2190 \quad (76)$$
(c) Longitudinal load force in the relative plane of upright 2006:
$$2180 + 2140 - 2170 - 2130 \quad (77)$$

Figure 21:
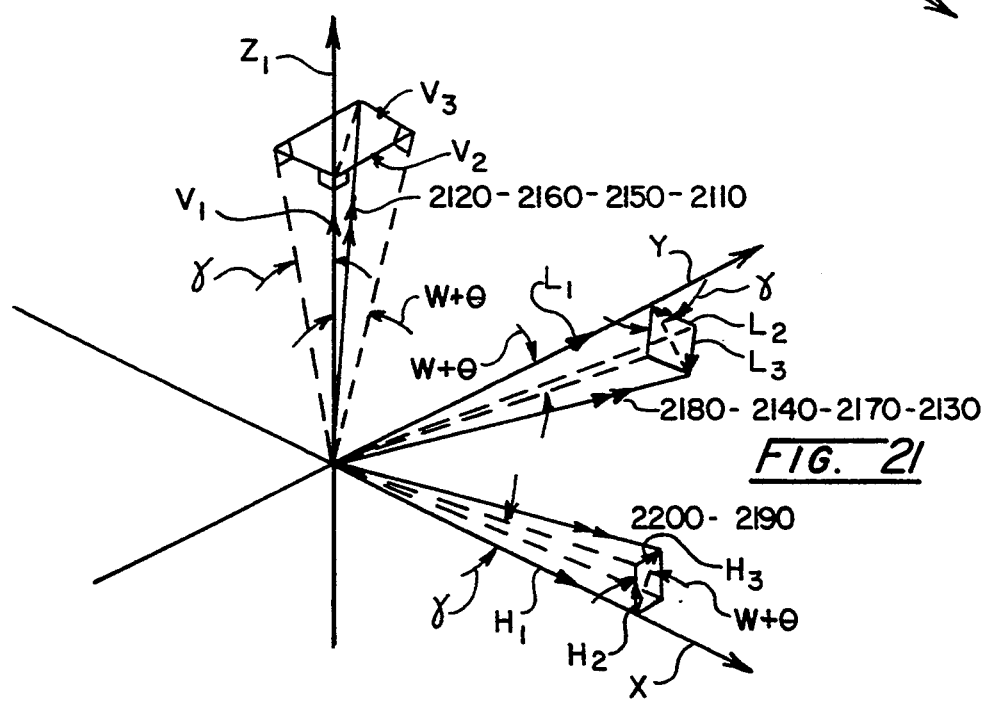
FIG. 21 is a free body diagram showing the construction normalizing the force vectors of FIG. 20 with respect to coordinates axes defining the ground plane.

Assuming that axle 2004 neither toes in or out relative to the car centerline, the load forces expressed in Eqs. 75–77 may be related to the ground plane through attitude angle $\theta$ and camber $\gamma$, which angles may be determined may be determined as explained in connection with FIGS. 4 and 5. Additionally, assuming an angular rotation of upright 2006, upon a relative movement of wheel 2002 with respect to the chassis, another angle, $\omega$, may be defined as the angular rotation of upright 2006 relative to the longitudinal direction of the ground plane. Rotation angle co may be determined, for example, from an established plot of $\omega$, measured relative to the ground plane, versus the angular deviation, 6, of a suspension element member, such as an A-arm, relative to the chassis. With angles $\theta$, $\gamma$, and $\omega$ thus defined, and with reference to FIG. 21 wherein the forces derived from FIG. 20 are shown relative to the ground plane defined by the reference coordinate axis X in the lateral direction, axis Y in the longitudinal direction, and axis Z in the vertical direction, the following normalized load force components resolved from Eqs. 75–77 may be determined:

(a) Vertical load force, $V_1$, in the ground plane derived from the vertical load force of Eq. 75:
$$\text{Eq. } 75/\sqrt{(((1 + (\tan \gamma)^2 + (\tan (\omega + \theta))^2)} \quad (78)$$
(b) Longitudinal load force, $V_2$, in the ground plane derived from the vertical load force of Eq. 75:
$$((\text{Eq. } 75)\tan (\omega + \theta))/\sqrt{(((1 + (\tan \gamma)^2 + (\tan (\omega + \theta))^2)} \quad (79)$$
(c) Lateral load force, $V_3$, in the ground plane derived from the vertical load force of Eq. 75:
$$-((\text{Eq. } 75)\tan\gamma)/\sqrt{(((1 + (\tan \gamma)^2 + (\tan (\omega + \theta))^2)} \quad (80)$$
(d) Longitudinal load force, $L_1$, in the ground plane derived from the longitudinal load force of Eq. 77:
$$\text{Eq. } 77/(\tan(\omega + \theta) \sqrt{(1/(\cos \gamma)^2 + 1/(\sin(\omega + \theta))^2 - 1)}) \quad (81)$$
(e) Lateral load force, $L_2$, in the ground plane derived from the longitudinal load force of Eq. 77:
$$\text{Eq. } 77 (\tan \gamma)/\sqrt{(1/(\cos \gamma)^2 + 1/(\sin(\omega + \theta))^2 - 1)} \quad (82)$$
(f) Vertical load force, $L_3$, in the ground plane derived from the longitudinal load force of Eq. 77:
$$-(\text{Eq. } 77)/\sqrt{(1/(\cos \gamma)^2 + 1/(\sin (\omega + \theta))^2 - 1)} \quad (83)$$
(g) Vertical load force, $H_2$, in the ground plane derived from the lateral load force of Eq. 76:
$$\text{Eq. } 76/\sqrt{(1/(\sin \gamma)^2 + 1/(\cos (\omega + \theta))^2 - 1)} \quad (84)$$
(h) Lateral load force, $H_1$, in the ground plane derived from the lateral load force of Eq. 76:
$$\text{Eq. } 76/(\tan \gamma \sqrt{(1/(\sin \gamma)^2 + 1/(\cos (\omega + \theta))^2 - 1)}) \quad (85)$$
(i) Longitudinal load force, $H_3$, in the ground plane derived from the lateral load force of Eq. 76:
$$\text{Eq. } 76 (\tan (\omega + \theta))/\sqrt{(1/(\sin \gamma)^2 + 1/(\cos (\omega + \theta))^2 - 1)} \quad (86)$$

With the vertical, lateral, and longitudinal components of the normalized forces being given by Eqs. 78–86, the total summed instantaneous grip forces within the contact patch at the interface of wheel 2002 and the ground plane therefore may be expressed as follows:

(a) Total load force in the vertical direction Z of the ground plane:
$$V_1 + L_3 + H_2 \quad (87)$$
(b) Total load force in the longitudinal direction Y of the ground plane:
$$V_2 + L_1 + H_3 \quad (88)$$
(c) Total load force in the lateral direction X of the ground plane:
$$V_3 + L_2 + H_1 \quad (89)$$

Figure 22A:
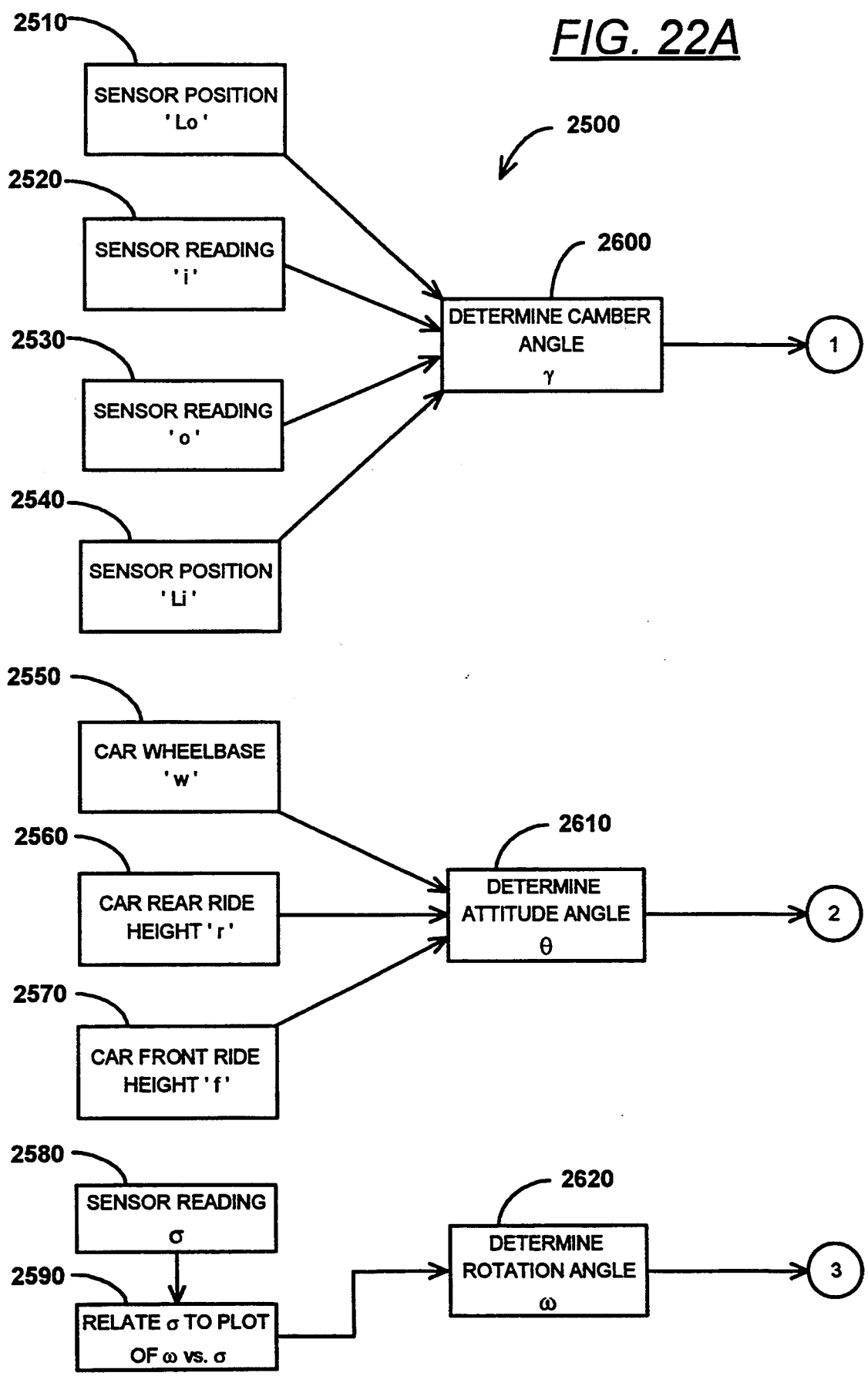
FIGS. 22A–B show a block schematic diagram of a representative arrangement of operations for analyzing the forces shown in the free body diagrams of FIG. 20 and 21.
Figure 22B:
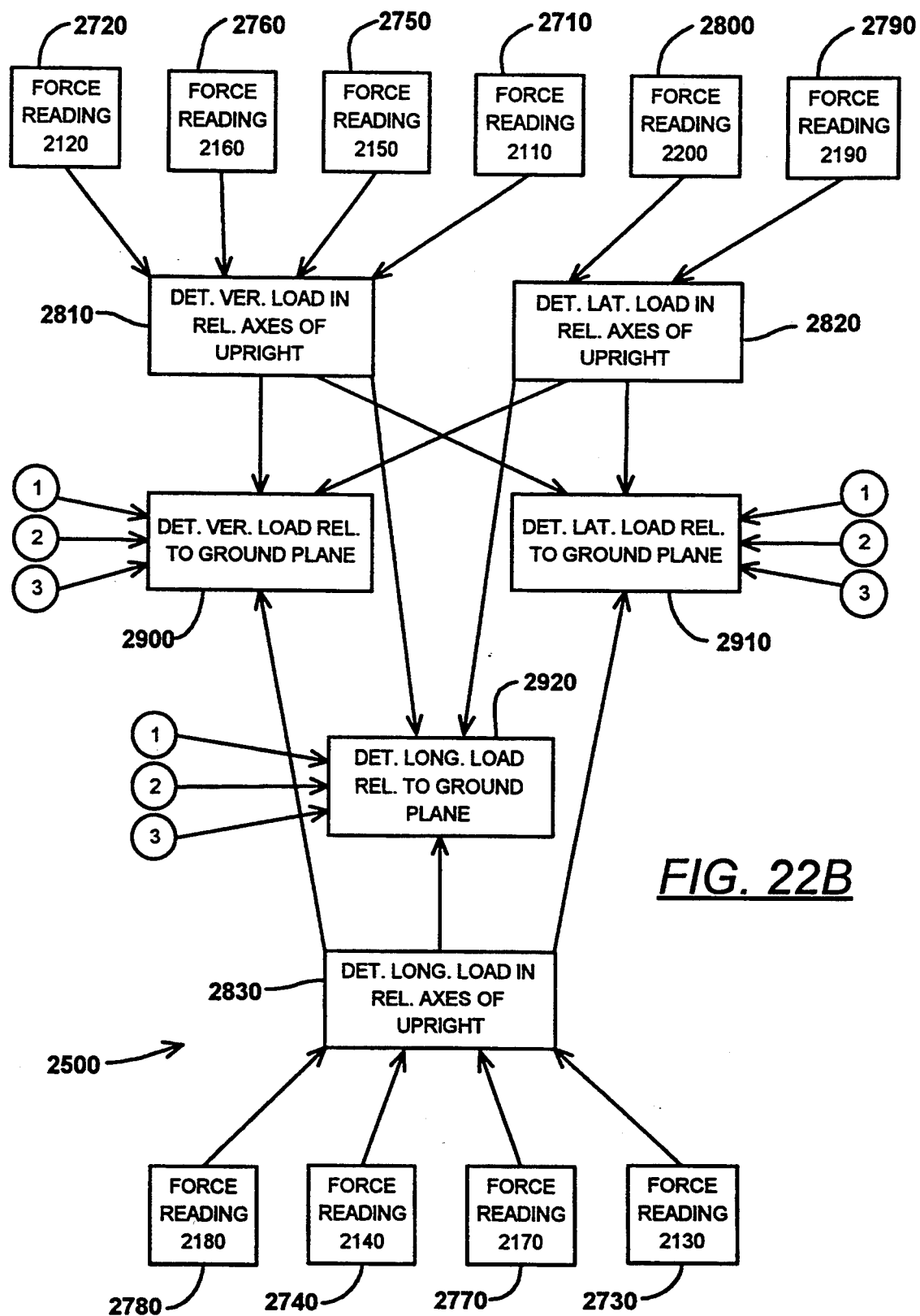

Turning to FIGS. 22A and 22B, the operations detailed in Eqs. 75–89 are shown in block diagrammatic form generally at 2500. In diagram 2500, input parameters or sensor reading inputs are received at blocks 2510, 2520, 2530, 2540, 2550, 2560, 2570, and 2580 as, respectively, the values or readings designated, "$L_o$", "i", "o", "$L_i$", "w", "r", "f", and "o". In turn, block 2600 receives inputs "$L_o$", "i", "o", and "$L_i$" for determining camber angle y, and block 2610 receives inputs "w", "r", and "f" for determining attitude angle $\theta$. From block 2580, angular deviation o is received by block 2590 for relation to an established plot of rotation angle co versus 6, which relation is received by block 2620 for determination of rotation angle co.

Sensor reading inputs are also received blocks 2720, 2760, 2750, 2710, 2800, 2790, 2780, 2740, 2770, and 2730 as respectively, load forces 2120, 2160, 2150, 2110, 2200, 2190, 2180, 2740, 2770, and 2730. From blocks 2720, 2760, 2750, and 2710, load forces 2120, 2160, 2150, and 2110 are received by block 2810 wherein the vertical load in the relative axes of upright 2006 (FIG. 19) is determined. In like manner, from blocks 2800 and 2790, load forces 2200 and 2190 are received by block 2820 wherein the lateral load in the relative axes of the upright is determined. Similarly, block 2830 receives load forces. 2180, 2140, 2170, and 2130 from, respectively, blocks 2780, 2740, 2770, and 2730 for determining the longitudinal load forces relative to the axes of the upright.

Next, blocks 2900, 2910, and 2920 are defined as receiving, respectively, the relative vertical load forces from block 2810, the relative lateral load forces from block 2820, and the relative longitudinal load forces from block 2830, each for relation to the ground plane. In this regard, blocks 2900, 2910, and 2920 each receive angles $\gamma$, $\theta$, and $\omega$ from, respectively, blocks 2600, 2610, and 2620. Thus arranged, the operations defined by Eqs. 75–89 may be used to derive the total vertical, lateral, and longitudinal instantaneous grip forces within the contact patch at the interface of wheel 2002 and the ground plane.

Since certain changes may be made in the above-described system and method without departing from the scope of the invention herein involved, it is intended that a, 11 matter contained in the description thereof or shown in the accompanying drawings shall be interpreted as illustrative and not in a limiting sense.

What is claimed:

1. A method for measuring a grip force between at least one wheel of a vehicle and a ground surface which defines a ground plane at said wheel, said wheel having a vertical and an axial centerline and being mounted on an upright, and said vehicle extending between a forward and a rearward portion along a longitudinal centerline and having a chassis extending between said forward and said rearward portion, said chassis having a lower surface defining a bottom plane of said vehicle and being supported on said wheel by at least one support member which is subjected to an instantaneous load force vector, said method comprising the steps of:
   (a) measuring a magnitude and relative direction of an instantaneous load force vector acting on each said support member supporting said chassis on said wheel;
   (b) resolving with respect to a relative plane each load force vector of step (a) into a first load force component, a second load force component normal to said first component, and a third load force component normal to said first and said second component;
   (c) relating each said first load force component to a reference plane to derive a first normalized load force component;
   (d) relating each said second load force component to said reference plane to derive a second normalized load force component normal to said first normalized load force component;
   (e) relating each said third load force component to said reference plane to derive a third normalized load force component normal to said first and said second normalized load force component; and
   (f) summing said normalized first, second, and third load force components to derive total normalized first, second, and third load force components which correspond to an instantaneous grip force developed between said wheel and said ground surface.

2. The method of claim 1 wherein said vehicle has at least one drive wheel and which further comprises the step of:
   (i) returning to step (a) of the method to derive total normalized lateral, longitudinal, and vertical load forces at each wheel of said vehicle.

3. The method of claim 1 wherein:
   said reference plane is said ground plane;
   each said first normalized load force component is derived as a lateral load force component in said ground plane directed transverse to the longitudinal centerline of said vehicle;
   each said second normalized load force component is derived as a longitudinal load force component in said ground plane directed parallel to the longitudinal centerline of said vehicle; and
   each said third normalized load force component is derived as a vertical load force component directed perpendicular to said ground plane.

4. The method of claim 3 further comprising the steps before step (c) of:
   determining an attitude angle between said bottom plane of said vehicle and said ground plane; and
   relating said attitude angle to said first, second, and third load force components for deriving said lateral, longitudinal, and vertical load force components.

5. The method of claim 3 further comprising the steps before step (c) of:
   determining a roll angle between said bottom plane of said vehicle and said ground plane; and
   relating said roll angle to said first, second, and third load force components for deriving said lateral, longitudinal, and vertical load force components.

6. The method of claim 3 further comprising the steps before step (c) of:
   determining a camber angle between the vertical centerline of said wheel and a line directed perpendicular to said ground plane; and
   relating said camber angle to said first, second, and third load force components for deriving said lateral, longitudinal, and vertical load force components.

7. The method of claim 3 further comprising the steps before step (c) of:
   measuring an instantaneous distance between at least one said support member and said ground plane; and
   relating said instantaneous distance to said first, second, and third load force components for deriving said lateral, longitudinal, and vertical load force components.

8. The method of claim 3 further comprising the steps before step (c) of:
   measuring an instantaneous distance between said upright and said ground plane; and
   relating said instantaneous distance to said first, second, and third load force components for deriving said lateral, longitudinal, and vertical load force components.

9. The method of claim 3 wherein said wheel is subjected to instantaneous centripetal and aerodynamic lift and drag forces and which further comprises the steps of:
   (i) determining with respect to said ground plane components of the centripetal forces on said wheel;
   (j) determining with respect to said ground plane components of the aerodynamic lift and drag forces on said wheel; and
   (k) relating the components of the forces of steps (i) and (j) to the load force components of step (f) to derive an absolute value of the load, aerodynamic, and centripetal forces acting upon said wheel.

10. A method for measuring a grip force between at least one wheel of a vehicle and a ground surface which defines a ground plane at said wheel, said wheel having a vertical and an axial centerline and being mounted on an upright, and said vehicle extending between a forward and a rearward portion along a longitudinal centerline and having a chassis extending between said forward and said rearward portion, said chassis having a lower surface defining a bottom plane of said vehicle and being supported on said wheel by at least one support member which is subjected to an instantaneous load force vector comprising at least one intermediate load member extending between a first end pivotally-coupled to said upright and a second end pivotally-coupled to said chassis, said method comprising the steps of:

(a) interposing a load isolation member between said first end of each said intermediate load member and said upright, each said load isolation member being configured as having a defined geometry isolating each said intermediate load member from said upright for measurement of the load force vectors acting on each said intermediate load member;

(b) measuring a magnitude and relative direction of an instantaneous load force vector acting on each said intermediate load member;

(c) resolving with respect to a relative plane each load force vector of step (b) into at least one load force component; and (d) summing said load force components to derive at least one total load force component which corresponds to an instantaneous grip force developed between said wheel and said ground surface.

11. The method of claim 10 wherein the support members supporting said chassis on said wheel further comprise a strutted piston member extending between a first end coupled to said upright and a second end coupled to said chassis, said piston member positioned to extend along a predetermined angle with respect to the vertical centerline of said wheel, said method further comprising the step prior to step (b) of:

interposing a load isolation member between said first end of said piston member and said upright, said load isolation member being configured as having a defined geometry isolating said piston member from said upright for measurement of the load force vectors acting on said piston member.

12. The method of claim 10 further comprising the steps before step (c) of:

measuring at least one instantaneous distance between said upright and said ground plane; and relating said instantaneous distance to said load force components for deriving said load force components normalized to said ground plane.

13. The method of claim 1 wherein said vehicle further comprises an axle having a first end supporting said wheel and a second end received by said upright, each said support member extending between said upright and said chassis.

14. A method for measuring a grip force between at least one wheel of a vehicle and a ground surface which defines a ground plane at said wheel, said wheel having a vertical and an axial centerline and being mounted on an upright, and said vehicle extending between a forward and a rearward portion along a longitudinal centerline and having a chassis extending between said forward and said rearward portion, said chassis having a lower surface defining a bottom plane of said vehicle and being supported on said wheel by at least one support member which is subjected to an instantaneous load force vector comprising at least one intermediate load member extending between a first end pivotally-coupled to said upright and a second end pivotally-coupled to said chassis, said method comprising the steps of:

(a) interposing a load isolation member between said second end of each said intermediate load member and said chassis, each said load isolation member being configured as having a defined geometry isolating each said intermediate load member from said chassis for measurement of the load force vectors acting on each said intermediate load member;

(b) measuring a magnitude and relative direction of an instantaneous load force vector acting on each said intermediate load member;

(c) resolving with respect to a relative plane each load force vector of step (b) into at least one load force component; and (d) summing said load force components to derive at least one total load force component which corresponds to an instantaneous grip force developed between said wheel and said ground surface.

15. The method of claim 14 further comprising the steps before step (c) of:

measuring at least one instantaneous distance between said chassis and said ground plane; and relating said instantaneous distance to said load force components for deriving said load force components normalized to said ground plane.

16. A method for measuring a grip force between at least one wheel of a vehicle and a ground surface which defines a ground plane at said wheel, said wheel being mounted on an upright and having a vertical and an axial centerline and an axle having a first end supporting said wheel and a second end received by said upright, and said vehicle extending between a forward and a rearward portion along a longitudinal centerline an having a chassis extending between said forward and said rearward portion, said chassis having a lower surface defining a bottom plane of said vehicle and being supported on said wheel by at least one support member which is subjected to an instantaneous load force vector, said method comprising the steps of:

(a) interposing a load carrier member intermediate said upright and said axle, said load carrier member being configured as having a defined geometry for measurement of a magnitude and relative direction of an instantaneous load forces acting between said axle and said upright;

(b) measuring a magnitude and relative direction of at least one instantaneous load force vector acting on said load carrier member; and (c) resolving with respect to a relative plane the load force vector of step (b) into at least one load force component corresponding to an instantaneous grip force developed between said wheel and said ground surface.

17. The method of claim 16 further comprising the steps before step (c) of:

measuring at least one instantaneous distance between said upright and said ground plane; and relating said instantaneous distance to said load force components for deriving said load force components normalized to said ground plane.

18. A system for measuring a grip force between at least one wheel of a vehicle and a ground surface which defines a ground plane at said wheel, said wheel having a vertical and an axial centerline and being mounted on an upright, and said vehicle extending between a forward and a rearward portion along a longitudinal centerline and having a chassis extending between said forward and said rearward portion, said chassis having a lower surface defining a bottom plane of said vehicle and being supported on said wheel by at least one support member which is subjected to an instantaneous load force vector, said system comprising:

at least one force sensor for providing load force output signals corresponding to a magnitude and relative direction of an instantaneous load force vector acting on each said support member supporting said chassis on said wheel; and a processor responsive to said load force output signals for resolving with respect to a relative plane each said force vector into a first load force component, a second load force component normal to said first component, and a third load force component normal to said first and said second component, for relating each said first load force component to a reference plane to derive a first normalized load force component, for relating each said second load force component to said reference plane to derive a second normalized load force component normal to said first normalized load force component, for relating each said third load force component to said reference plane to derive a third normalized load force component normal to said first and said second normalized load force component, and for summing said normalized first, second, and third load force components to derive total normalized first, second, and third load force components which correspond to an instantaneous grip force developed between said wheel and said ground surface.

19. The system of claim 18 wherein said vehicle has at least one drive wheel and further comprising at least one force sensor at each wheel of said vehicle, for providing additional load force output signals corresponding to a magnitude and relative direction of an instantaneous load force vector acting on each support member supporting said chassis on each wheel of said vehicle, said processor being further responsive to said additional load force output signals to derive total normalized lateral, longitudinal, and vertical load forces at each wheel of said vehicle.

20. The system of claim 18 wherein:
said reference plane is said ground plane;
each said first normalized load force component is derived as a lateral load force component in said ground plane directed transverse to the longitudinal centerline of said vehicle;
each said second normalized load force component is derived as a longitudinal load force component in said ground plane directed parallel to the longitudinal centerline of said vehicle; and
each said third normalized load force component is derived as a vertical load force component directed perpendicular to said ground plane.

21. The system of claim 18 wherein said vehicle further comprises an axle having a first end supporting said wheel and a second end received by said upright, each said support member extending between said upright and said chassis.

22. The system of claim 20 further comprising:
a pair of distance sensors respectively mounted on said chassis at a first forward point and a second rearward point for providing distance output signals corresponding to the distance at two points along said chassis between said bottom plane of said vehicle and said ground plane, said processor being further responsive to said distance output signals for deriving an attitude angle between said bottom plane and said ground plane, and for relating said first, second, and third load force components to said attitude angle for deriving said lateral, longitudinal, and vertical load force components.

23. The system of claim 20 further comprising:
at least a pair of distance sensors mounted on the upright of said wheel for providing distance output signals corresponding to the distance from said upright to said ground plane, said processor being further responsive to said distance output signals for deriving a camber angle between the vertical centerline of said wheel and a line directed perpendicular to said ground plane, and for relating said first, second, and third load force components to said camber angle for deriving said lateral, longitudinal, and vertical load force components.

24. The system of claim 20 further comprising:
a pair of distance sensors mounted on said chassis generally transverse to the longitudinal centerline of said vehicle for providing distance output signals corresponding to the distance at two points along said chassis between said bottom plane of said vehicle and said ground plane, said processor being further responsive to said distance output signals for deriving a roll angle between said bottom plane and said ground plane, and for relating said first, second, and third load force components to said roll angle for deriving said lateral, longitudinal, and vertical load force components.

25. The system of claim 20 further comprising:
at least one distance sensor mounted on at least one of the support members supporting said chassis on said wheel for providing distance output signals corresponding to the distance between the support member and said ground plane, said processor being further responsive to said distance output signals for relating said first, second, and third load force components thereto for deriving said lateral, longitudinal, and vertical load force components.

26. The system of claim 20 further comprising:
at least one distance sensor mounted on said upright for providing distance output signals corresponding to the distance between said upright and said ground plane, said processor being further responsive to said distance output signals for relating said first, second, and third load force components thereto for deriving said lateral, longitudinal, and vertical load force components.

27. A system for measuring a grip force between at least one wheel of a vehicle and a ground surface which defines a ground plane at said wheel, said wheel having a vertical and an axial centerline and being mounted on an upright, and said vehicle extending between a forward and a rearward portion along an longitudinal centerline and having a chassis extending between said forward and said rearward portion, said chassis having a lower surface defining a bottom plane of said vehicle and being supported on said wheel by at least one support member which is subjected to on instantaneous load force vector comprising at least one intermediate load member extending between a first end pivotally-coupled to said upright and a second end pivotally-coupled to said chassis, said system comprising:
- a load isolation member interposed between said first end of each said intermediate member and said upright, each said load isolation member being configured as having a defined geometry isolating each said intermediate load member from said upright;
- at least one force sensor interposed between each said load isolation member and said upright for providing load force output signals corresponding to a magnitude and relative direction of an instantaneous load force vector acting on each said intermediate member; and
- a processor responsive to said load force output signals for resolving with respect to a relative plane each said force vector into at least one load force component, and for summing said load force components to derive at least one total load force component which corresponds to an instantaneous grip force developed between said wheel and said ground surface.

28. The system of claim 27 wherein the intermediate load members extending between said upright and said chassis include a strutted piston member extending between a first end coupled to said upright and a second end coupled to said chassis, said piston member positioned to extend along a predetermined angle with respect to the vertical centerline of said wheel, said system further comprising:
- a load isolation member interposed between said first end of said piston member and said upright, said load isolation member being configured as having a defined geometry isolating said piston member from said upright; and
- at least one force sensor interposed between said load isolation member and said upright for providing said force output signals to said processor corresponding to a magnitude and relative direction of an instantaneous load force vector acting on said piston member.

29. The system of claim 27 further comprising:
- at least a pair of distance sensors mounted on the upright of said wheel for providing distance output signals corresponding to the distance from at least two points on said upright to said ground plane, said processor being further responsive to said distance output signals for relating said load force components thereto for deriving said load force components normalized to said ground plane.

30. A system for measuring a grip force between at least one wheel of a vehicle and a ground surface which defines a ground plane at said wheel, said wheel having a vertical and an axial centerline and being mounted on an upright, and said vehicle extending between a forward and a rearward portion along a longitudinal centerline and having a chassis extending between said forward and said rearward portion, said chassis having a lower surface defining a bottom plane of said vehicle and being supported on said wheel by at least one support member which is subjected to an instantaneous load force vector comprising at least one intermediate load member extending between a first end pivotally-coupled to said upright and a second end pivotally-coupled to said chassis, said system comprising:
- a load isolation member interposed between said second end of each said intermediate member and said chassis, each said load isolation member being configured as having a defined geometry isolating each said intermediate load member from said chassis;
- at least one force sensor interposed between each said second load isolation member and said chassis for providing load force output signals corresponding to a magnitude and relative direction of an instantaneous load force vector acting on each said intermediate member; and
- a processor responsive to said load force output signals for resolving with respect to a relative plane each said force vector into at least one load force component, and for summing said load force components to derive at least one total load force component which corresponds to an instantaneous grip force developed between said wheel and said ground surface.

31. The system of claim 30 further comprising:
- at least a pair of distance sensors mounted on said chassis for providing distance output signals corresponding to the distance from at least two points along said chassis from said bottom plane of said vehicle to said ground plane, said processor being further responsive to said distance output signals for relating said load force components thereto for deriving said load force components normalized to said ground plane.

32. A system for measuring a grip force between at least one wheel of a vehicle and a ground surface which defines a ground plane at said wheel, said wheel being mounted on an upright and having a vertical and an axial centerline and an axle having a first end supporting said wheel and a second end received by said upright, and said vehicle extending between a forward and a rearward portion along a longitudinal centerline and having a chassis extending between said forward and said rearward portion, said chassis having a lower surface defining a bottom plane of said vehicle and being supported on said wheel by at least one support member which is subjected to an instantaneous load force vector, said system comprising:
- a load carder member interposed between said upright and said axle, said load carrier member being configured as having a defined geometry for measurement of a magnitude and relative direction of an instantaneous load forces acting between said axle and said upright;
- at least one force sensor interposed between said load carrier member and said upright for providing load force output signals corresponding to a magnitude and relative direction of at least one instantaneous load force vector acting between said axle and said upright; and
- a processor responsive to said load force output signals for resolving with respect to a relative plane said load force vector into at least one load force component corresponding to an instantaneous grip force developed between said wheel and said ground surface.

33. The system of claim 32 further comprising:
- at least a pair of distance sensors mounted on the upright of said wheel for providing distance output signals corresponding to the distance from at least two points on said upright to said ground plane, said processor being further responsive to said distance output signals for relating said load force component thereto for deriving said load force component normalized to said ground plane.

* * * * *